(12) United States Patent
Tanaka et al.

(10) Patent No.: US 10,671,678 B2
(45) Date of Patent: *Jun. 2, 2020

(54) SURFACE ACOUSTIC WAVE SENSOR

(71) Applicants: KYOCERA CORPORATION, Kyoto (JP); OSAKA UNIVERSITY, Osaka (JP)

(72) Inventors: Hiroyasu Tanaka, Kyoto (JP); Hideharu Kurioka, Kyoto (JP); Eiichi Tamiya, Osaka (JP); Masato Saito, Osaka (JP)

(73) Assignees: KYOCERA CORPORATION, Kyoto (JP); OSAKA UNIVERSITY, Osaka (JP)

( * ) Notice: Subject to any disclaimer, the term of this patent is extended or adjusted under 35 U.S.C. 154(b) by 5 days.

This patent is subject to a terminal disclaimer.

(21) Appl. No.: 16/036,574

(22) Filed: Jul. 16, 2018

(65) Prior Publication Data

US 2018/0341707 A1  Nov. 29, 2018

Related U.S. Application Data

(63) Continuation of application No. 14/438,844, filed as application No. PCT/JP2013/070808 on Jul. 31, 2013, now Pat. No. 10,037,382.

(30) Foreign Application Priority Data

Oct. 29, 2012  (JP) .................................. 2012-237819

(51) Int. Cl.
*G06F 16/951* (2019.01)
*G06F 16/954* (2019.01)
(Continued)

(52) U.S. Cl.
CPC ............ *G06F 16/951* (2019.01); *A61P 35/00* (2018.01); *C07F 9/564* (2013.01); *G01N 29/022* (2013.01);
(Continued)

(58) Field of Classification Search
CPC ..... G01N 29/022; G06F 3/04842; H03H 9/25
See application file for complete search history.

(56) References Cited

U.S. PATENT DOCUMENTS

| 5,130,257 | A | * | 7/1992 | Baer | ..................... | G01N 29/022 |
| | | | | | | 204/400 |
| 10,037,382 | B2 | * | 7/2018 | Tanaka | ................... | G01N 29/022 |
| 2005/0112672 | A1 | * | 5/2005 | Benson | ................... | B82Y 30/00 |
| | | | | | | 435/6.12 |

FOREIGN PATENT DOCUMENTS

| JP | 2006-162318 A | 6/2006 |
| JP | 2006-184011 A | 7/2006 |

(Continued)

OTHER PUBLICATIONS

Publication dated Jul. 31, 2013 and International Search Report dated Oct. 3, 2013, from related International Patent Application No. PCT/JP2013/070808.

*Primary Examiner* — Thomas M Dougherty
*Assistant Examiner* — Karen B Addison
(74) *Attorney, Agent, or Firm* — Duane Morris LLP

(57) ABSTRACT

The present invention provides a surface acoustic wave sensor capable of suitably controlling the flow of a liquid sample onto IDT electrodes. A surface acoustic wave sensor has a piezoelectric substrate, a first IDT electrode and a second IDT electrode which are located on the upper surface of the piezoelectric substrate and are separated from each other while sandwiching a detection part on the piezoelectric substrate therebetween, and the cover which forms the space being on the first IDT electrode, second IDT electrode, and (Continued)

the detection part and straddling them. On the lower surface of the cover, the detection part-facing surface facing the detection part has a smaller contact angle to the liquid sample than that of a pair of electrode-facing surfaces facing the first IDT electrode and second IDT electrode.

21 Claims, 12 Drawing Sheets

(51) Int. Cl.
| | |
|---|---|
| *H03H 9/25* | (2006.01) |
| *A61P 35/00* | (2006.01) |
| *G01N 29/02* | (2006.01) |
| *G01N 29/22* | (2006.01) |
| *G06F 40/134* | (2020.01) |
| *G06F 3/0484* | (2013.01) |
| *H03H 9/02* | (2006.01) |
| *H03H 9/10* | (2006.01) |
| *C07F 9/564* | (2006.01) |

(52) U.S. Cl.
CPC ....... *G01N 29/222* (2013.01); *G06F 3/04842* (2013.01); *G06F 16/954* (2019.01); *G06F 40/134* (2020.01); *H03H 9/02622* (2013.01); *H03H 9/1092* (2013.01); *H03H 9/25* (2013.01); *C07B 2200/07* (2013.01); *G01N 2291/0255* (2013.01); *G01N 2291/0256* (2013.01); *G01N 2291/0423* (2013.01)

(56) References Cited

FOREIGN PATENT DOCUMENTS

| | | | | |
|---|---|---|---|---|
| JP | 2007-010378 | A | 1/2007 | |
| JP | 2008-157708 | A | 7/2008 | |
| JP | 2009-150754 | A | 7/2009 | |
| JP | 2006-162318 | * | 9/2012 | ............ G01N 29/24 |
| JP | 2012-181093 | A | 9/2012 | |
| WO | WO-2010-073484 | A1 | 7/2010 | |

* cited by examiner

SURFACE ACOUSTIC WAVE SENSOR

RELATED APPLICATIONS

This application is a Continuation application of U.S. patent application Ser. No. 14/438,844, filed Apr. 27, 2015, which is a U.S. National Phase Application of PCT/JP2013/070808, filed on Jul. 31, 2013, which claims the benefit of the filing date of Japanese Application No. 2012-237819, filed Oct. 29, 2012. The contents of these earlier-filed applications are hereby incorporated by reference herein in their entireties.

TECHNICAL FIELD

The present invention relates to a surface acoustic wave sensor which is capable of measuring a property of a liquid or an ingredient which is contained in the liquid. Note that, the liquid need only have fluidity. It does not matter even if its viscosity is high.

BACKGROUND ART

Known in the art is a surface acoustic wave sensor which uses a surface acoustic wave element to measure the property of a liquid sample or ingredients of a liquid sample.

A surface acoustic wave sensor is comprised of a piezoelectric substrate on which is provided a detection part which reacts with an ingredient contained in a liquid sample on. It measures an electric signal based on a surface acoustic wave (SAW) which is propagated through this detection part to there by detect a property or an ingredient of the liquid sample.

A SAW is generated by an IDT electrode comprised of a pair of comb-shaped electrodes which are provided on an upper surface of the piezoelectric substrate. To prevent the IDT electrode from being immersed in the liquid sample, it is known to provide a sealing member which forms a closed space over the IDT electrode (for example, Patent Literature 1).

The sealing member has a partition wall which is supported on the upper surface of the piezoelectric substrate between the IDT electrode and the detection part. Due to this, the flow of the liquid sample onto the IDT electrode is suppressed. In this way, conventionally, the flow of the liquid sample is controlled by a channel wall.

However, the control of the flow of the liquid sample by the channel wall causes various inconveniences. For example, the partition wall which is positioned between the IDT electrode and the detection part becomes a primary factor of propagation loss of the SAW when the SAW is propagated from the IDT electrode to the detection part.

Further, for example, if the liquid sample is allowed to flow onto the IDT electrode and the channel wall is positioned outside the detection part and the IDT electrode, the liquid sample running along the channel wall causes the liquid sample to flow on the IDT electrode prior to on the detection part. As a result, air bubbles were liable to form on the detection part.

Therefore, it has been desired to provide a surface acoustic wave sensor capable of suitably controlling the flow of a liquid sample.

CITATIONS LIST

Patent Literature

Patent Literature 1: Japanese Patent Publication No. 2006-184011A

SUMMARY OF INVENTION

A surface acoustic wave sensor according to one aspect of the present invention has a piezoelectric substrate, a detection part which is located on an upper surface of the piezoelectric substrate and detects a detection object which is contained in a sample, a pair of IDT electrodes which are located on the upper surface of the piezoelectric substrate while sandwiching the detection part there between, and a cover which covers the detection part and the pair of IDT electrodes through a space. A lower surface of the cover has a first region which faces the detection part and a pair of second regions which are located on the two sides relative to the first region in a direction of alignment of the detection part and the pair of IDT electrodes. The first region has a smaller contact angle to the sample than that of the pair of second regions.

According to the constitution described above, the flow of the liquid sample (liquid-state sample) can be suitably controlled. Note that, the sample (liquid sample), for example, may be one which contains water and may be one which contains oil. Further, for example, the sample may be a solution and may be sol.

DESCRIPTION OF EMBODIMENTS

Figure 1:
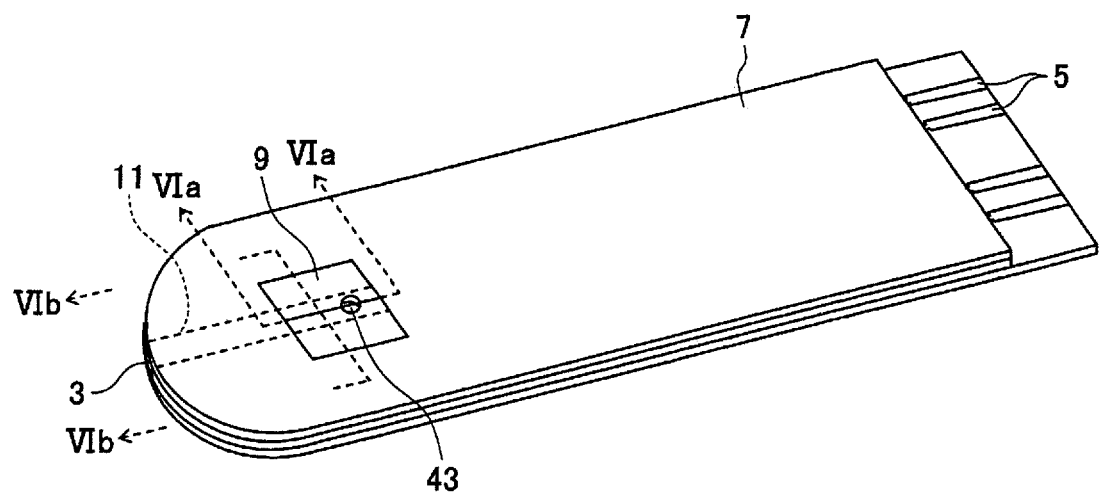
FIG. 1 is a perspective view showing a SAW sensor according to a first embodiment of the present invention.
Figure 1:
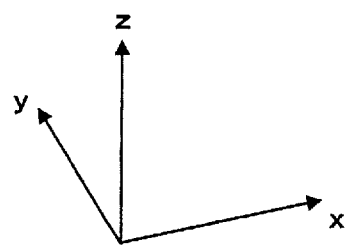

Below, embodiments of a SAW sensor according to the present invention will be explained in detail with reference to the drawings. Note that, in the drawings explained below, the same notations will be attached to the same components. Further, the sizes of the members and the distance between the members and so on will be diagrammatically shown and are sometimes different from the actual ones.

Further, in a SAW sensor, any direction may be made upward or downward. However, in the following description, conveniently an orthogonal coordinate system xyz is defined, and use is made of "upper surface", "lower surface", and other terms deeming the positive side of the z-direction as the upper part.

First Embodiment

FIG. 1 is a perspective view showing a SAW sensor 1 according to a first embodiment.

The SAW sensor 1 is for example formed in a roughly rectangular plate shape as a whole. The thickness thereof is for example 0.5 mm to 3 mm, the length in the x-direction is for example 1 cm to 5 cm, and the length in the y-direction is for example 1 cm to 3 cm.

The SAW sensor 1 is provided with a first inflow port 3 for taking in a liquid sample and a plurality of terminals 5 which are used for input/output of electric signals. The first inflow port 3 is for example positioned on one end of the rectangular shape, and the plurality of terminals 5 are for example positioned on the other end of the rectangular shape.

The SAW sensor 1 is for example attached to a not shown reader including an oscillation circuit etc. The attachment is for example carried out by inserting the end part on the terminal 5 side of the SAW sensor 1 into a slot of the reader. Then, the SAW sensor 1 changes an electric signal input from the reader to any of the plurality of terminals 5 in accordance with the property or ingredient of the liquid sample taken from the first inflow port 3 and outputs the result from any of the plurality of terminals 5 to the reader. The SAW sensor 1 is made for example a disposable SAW sensor.

The SAW sensor 1 has a base 7 and a sensor chip 9 which is mounted on the base 7. The sensor chip 9 substantially converts an electric signal in accordance with the liquid sample. The base 7 functions as a package which contributes to improvement of handle ability of the sensor chip 9 and so on.

In the base 7, the first inflow port 3 which is already explained and a passage 11 for guiding the liquid sample taken from the first inflow port 3 to the sensor chip 9 are formed. The passage 11 for example linearly extends from the first inflow port 3 to the sensor chip 9. Further, the base 7 has the plurality of terminals 5 which are already explained and wirings 13 connecting the plurality of terminals 5 and the sensor chip 9 (see FIG. 2).

Figure 2:
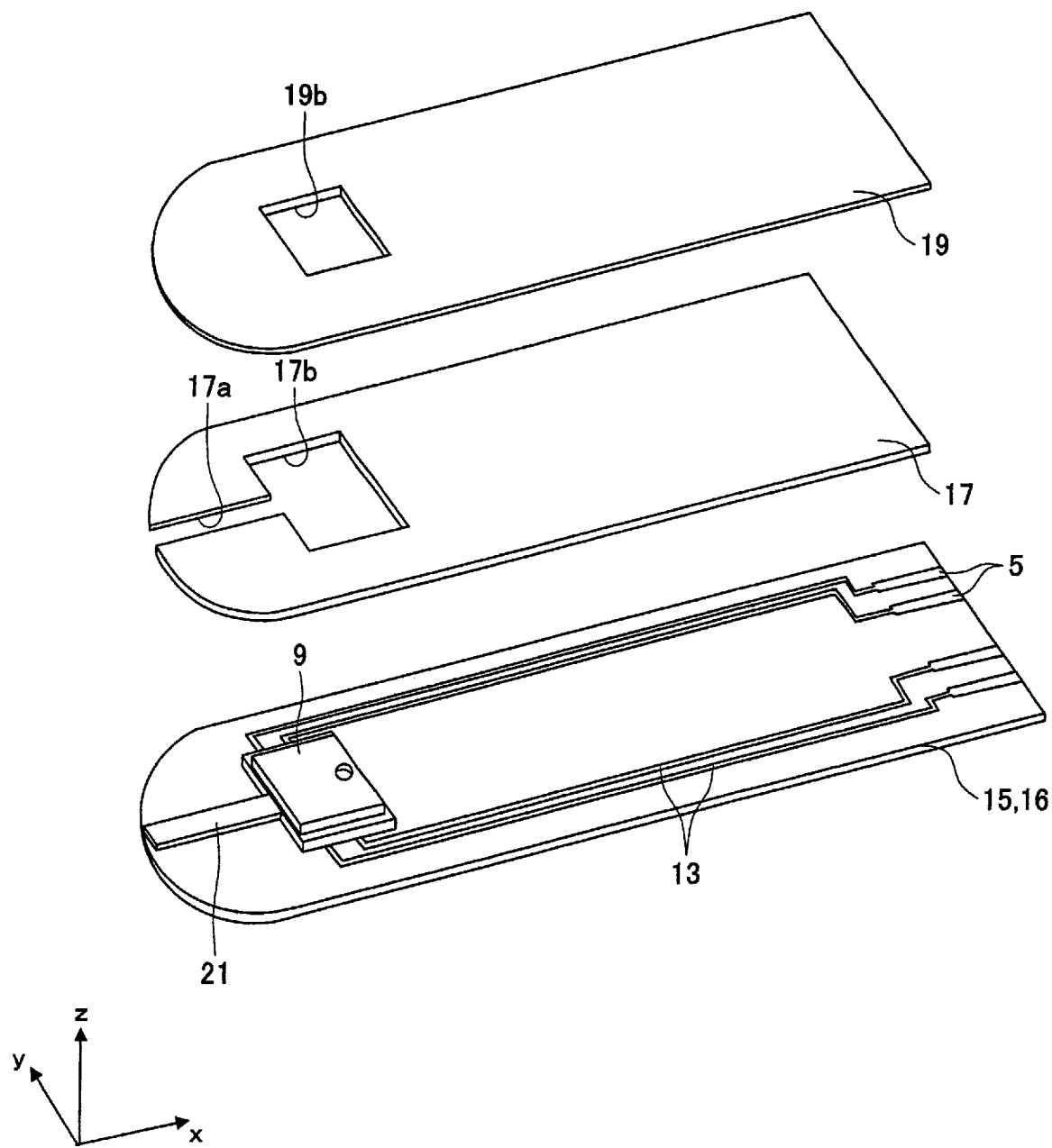
FIG. 2 is a disassembled perspective view of the SAW sensor in FIG. 1.

FIG. 2 is a disassembled perspective view of the SAW sensor 1.

The base 7 has for example a lower layer member 15, middle layer member 17, and upper layer member 19 which are stacked over each other.

The lower layer member 15 is for example configured the same constitution as a printed circuit board. An insulating base 16 thereof is for example comprised of a resin or ceramic as the main constituent. The planar shape of the insulating base 16 is for example the same as the planar shape of the SAW sensor 1 as a whole. On the upper surface of the insulating base 16, the already explained plurality of terminals 5 and wirings 13 are formed. The sensor chip 9 is for example fixed to the upper surface of the insulating base 16 by an adhesive agent.

The middle layer member 17 is for example comprised of a resin or ceramic or other insulating material. The middle layer member 17 is for example adhered to the lower layer member 15 by an adhesive agent. The planar shape of the middle layer member 17 is made a rectangle which is somewhat shorter than the lower layer member 15 so that the plurality of terminals 5 are exposed. Further, on one end side of the middle layer member 17, a cutout 17A for forming the first inflow port 3 and passage 11 and a first hole part 17B for accommodating the sensor chip 9 are formed. The cutout 17A and the first hole part 17B are connected.

The upper layer member 19 is comprised of for example a hydrophilic film. Accordingly, in the upper layer member 19, for example, the wettability with respect to the liquid sample becomes higher compared with the lower layer member 15 and middle layer member 17. Note that, the degree of the wettability (or hydrophilicity) with respect to the liquid sample can be measured by a contact angle to the liquid sample as is generally known. As the hydrophilic film, use can be made of a commercially available resin film subjected to a hydrophilic treatment. The resin is for example polyester based or polyethylene based. The upper layer member 19 is for example adhered to the middle layer member 17 by an adhesive agent. The planar shape of the upper layer member 19 is made a rectangle which is a bit shorter than the lower layer member 15 in the same way as the middle layer member 17. Further, in the upper layer member 19, a second hole part 19B for exposing the upper surface of the sensor chip 9 is formed.

Note that, the SAW sensor 1 for example does not have flexibility. For example, at least one of the lower layer member 15, middle layer member 17, and upper layer member 19 does not have flexibility.

When the lower layer member 15, middle layer member 17, and upper layer member 19 are stacked, by formation of the cutout 17A in the middle layer member 17, a passage 11 is formed between the upper surface of the lower layer member 15 and the lower surface of the upper layer member 19. Further, by formation of the first hole part 17B and second hole part 19B in the middle layer member 17 and upper layer member 19, a concave portion for accommodating the sensor chip 9 is constituted.

On the upper surface of the lower layer member 15, a bottom surface member 21 is provided at the position where the passage 11 is formed. The upper surface of the bottom surface member 21 forms the bottom surface of the passage 11. The bottom surface member 21 is for example formed by a hydrophilic film in the same way as the upper layer member 19. Accordingly, at the bottom surface member 21, the contact angle to the liquid sample becomes smaller than that at the lower layer member 15. The bottom surface member 21 is for example fixed to the upper surface of the lower layer member 15 by an adhesive agent 22 (see FIG. 6A).

In the passage 11, the height in the z-direction is set relatively small. For example, the height in the z-direction of the passage 11 is 50 μm to 0.5 mm. From the viewpoint of reducing the amount of the liquid sample (for example reducing the amount of collection of blood), the height of the passage 11 is preferably about 50 μm. Further, as explained above, at the ceiling surface of the passage 11 (upper surface of the passage 11, lower surface of the upper layer member 19) and the bottom surface (lower surface of the passage 11, upper surface of the bottom surface member 21), the contact angle to the liquid sample is small.

The height in the z-direction of the passage 11 is small, and the contact angle to the liquid sample is small at the ceiling surface etc. Therefore, when the liquid sample contacts the first inflow port 3, the liquid sample flows toward the sensor chip 9 in the passage 11 due to a capillary phenomenon. That is, in the base 7 of the present embodiment, work of using a micropipette or another implement to suck up the liquid sample and discharging the sucked up liquid sample into the first inflow port 3 is unnecessary.

Note that, the capillary phenomenon may occur if the contact angle of the inner surface of the passage is less than 90°. Accordingly, the wettability (hydrophilicity) of the upper layer member 19 and bottom surface member 21 (hydrophilic films) only have to be high to an extent where the contact angle to the liquid sample (this may be represented by water) becomes less than 90°. Further, from the viewpoint of reliably causing the capillary phenomenon, the wettability is preferably high enough so that the contact angle becomes less than 60°.

Figure 3:
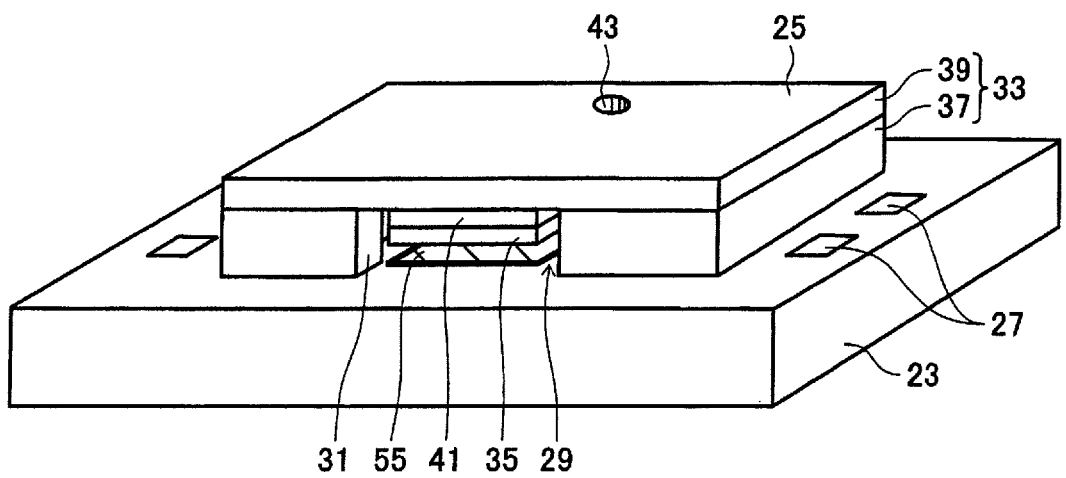
FIG. 3 is a perspective view showing a sensor chip of the SAW sensor in FIG. 1.
Figure 3:
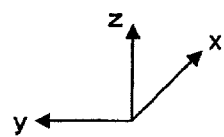
Figure 4:
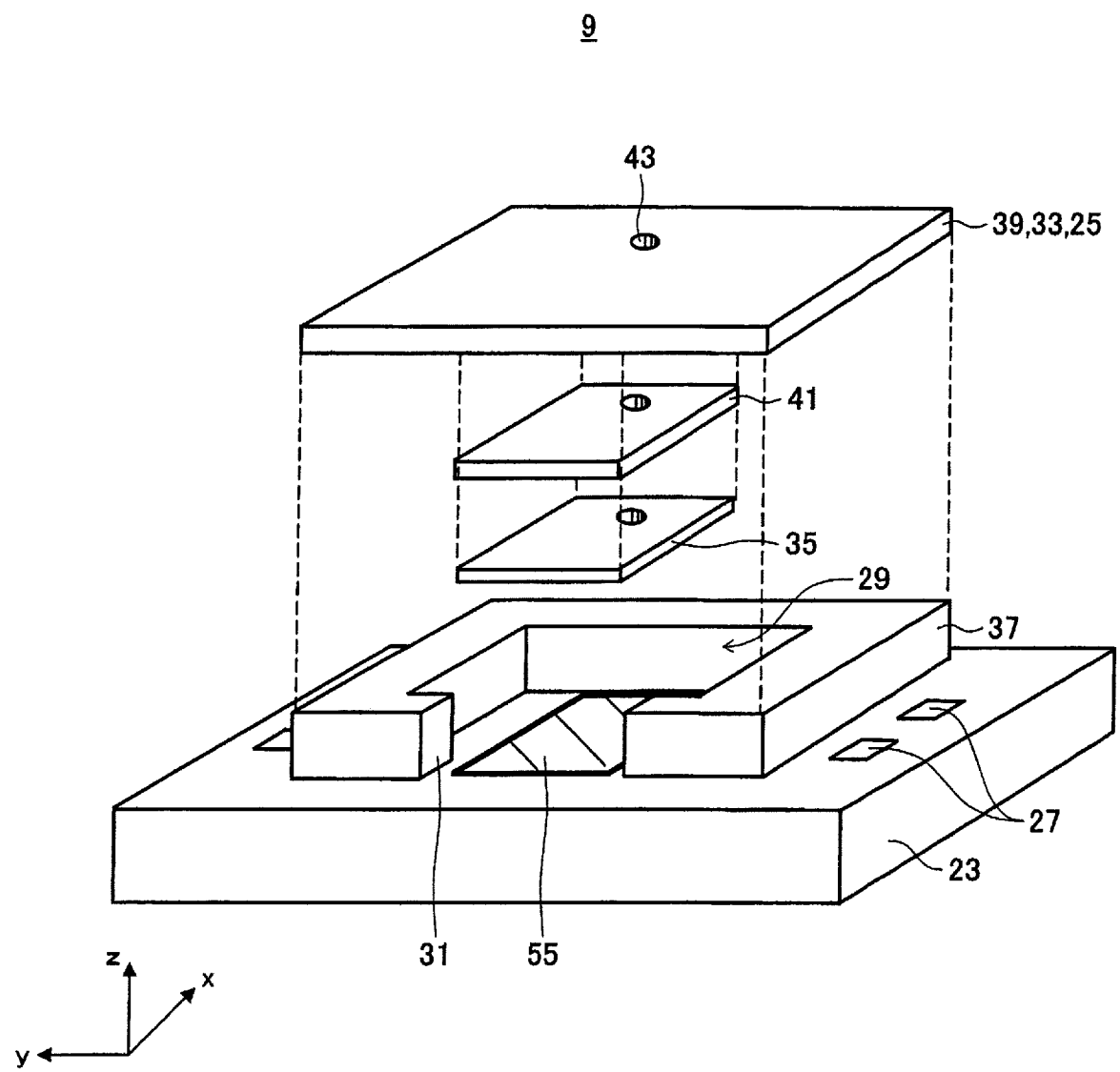
FIG. 4 is a disassembled perspective view showing a sensor chip in FIG. 3.

FIG. 3 is a perspective view of the sensor chip 9. Further, FIG. 4 is a disassembled perspective view of the sensor chip 9.

The sensor chip 9 has a piezoelectric substrate 23, a cover 25 which covers the piezoelectric substrate 23, and a plurality of pads 27 which are exposed to their outside and are provided for input/output of electric signals. Between the piezoelectric substrate 23 and the cover 25, a space 29 into which the liquid sample is introduced is formed. The space 29 is connected to the passage 11 of the base 7 through a second inflow port 31 which is opened in the side surface of the cover 25.

The piezoelectric substrate 23 is for example constituted by a substrate of a single crystal having piezoelectricity such as a lithium tantalate (LiTaO3) single crystal, lithium niobate (LiNbO3) single crystal, or quartz crystal. The planar shape and various dimensions of the piezoelectric substrate 23 may be suitably set. As an example, the thickness of the piezoelectric substrate 23 is 0.3 mm to 1 mm.

The cover 25 has a cover body 33 (base material) constituting the major part thereof and a film 35 which is adhered to the lower surface (ceiling surface) of the cover body 33.

The cover body 33 has a frame 37 which is located on the piezoelectric substrate 23 and a lid 39 which is located on the frame 37. An opening vertically penetrating through the frame 37 is closed from the top and the bottom by the piezoelectric substrate 23 and the lid 39. Due to this, the space 29 is formed. Further, the second inflow port 31 is formed by interruption of a portion of the frame 37. Note that, the frame 37 and the lid 39 may be formed integrally as well.

The cover body 33 is for example made of a resin or ceramic or other insulating material. Preferably, the cover body 33 is made of polydimethylsiloxane. By using polydimethylsiloxane, it is easy to give any shape to the cover body 33, for example, a shape having rounded corners. Further, if polydimethylsiloxane is used, it is relatively easy to form the ceiling portion and side walls of the cover body 33 thick. The thickness of the lid 39 and the width of the frame 37 (thickness of the side walls of the cover body 33) is for example 0.3 mm to 5 mm.

The film 35 is for example constituted by a hydrophilic film in the same way as the upper layer member 19 and bottom surface member 21. Accordingly, for example, the film 35 has a smaller contact angle to the liquid sample than the cover body 33. Further, the contact angle of the liquid sample on the lower surface thereof is less than 90°, preferably less than 60°. The film 35 is for example adhered to the lower surface of the cover body 33 by an adhesive agent 41. Note that, the film 35 may be adhered to the lower surface of the cover body 33 without use of the adhesive agent 41 by adhesion of the cover body 33 and/or film 35 itself.

In the cover 25, a through hole 43 contributing to evacuation etc. of the space 29 is formed. The through hole 43 is for example formed in the upper part of the cover 25 by formation of hole in each of the lid 39, adhesive agent 41, and film 35. This through hole 43 is exposed to the outside of the base 7 by the upper surface of the sensor chip 9 being exposed through the second hole part 19B of the upper layer member 19 to the outside of the base 7 (see FIG. 1 and FIG. 2). Accordingly, the space 29 is communicated with the outside of the SAW sensor 1 through the through hole 43. The through hole 43 is located on the side opposite to the second inflow port 31 with respect to the space 29.

The pads 27 are for example provided on the upper surface of the piezoelectric substrate 23 on the outside of the cover 25. Although not particularly shown, for example, the pads 27 are connected to the pads provided on the lower layer member 15 by bonding wires and consequently connected to the wirings 13.

The height in the z-direction of the space 29 (in more detail, the distance between a metal film 55 which will be explained later and the film 35) is set relatively small. For example, in the same way as the passage 11, the height is 50 μm to 0.5 mm and preferably about 50 μm. Further, on the ceiling surface of the space 29, in the same way as the ceiling surface etc. of the passage 11, the contact angle to the liquid sample is small due to the film 35. Accordingly, the liquid sample guided in the passage 11 to the second inflow port 31 due to the capillary phenomenon is introduced into the space 29 due to the capillary phenomenon.

When the liquid sample is introduced into the space 29, air which has originally existed in the space 29 is released to the outside through the through hole 43. Due to this, the liquid sample becomes easier to enter into the space 29. Note that, the through hole 43 can discharge air in the passage 11 and space 29 even at the time when the liquid sample flows in the passage 11.

Figure 5:
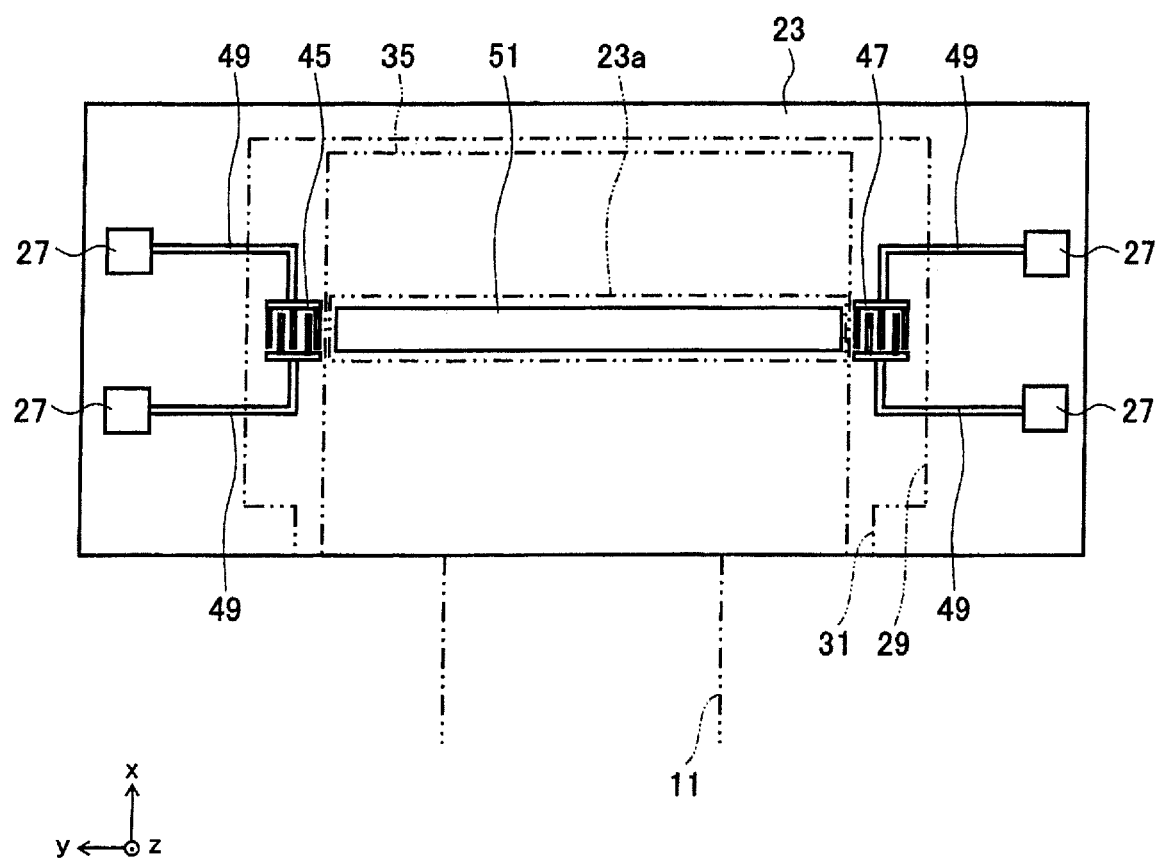
FIG. 5 is a plan view showing an upper surface of a piezoelectric substrate of the sensor chip in FIG. 3.

FIG. 5 is a plan view showing the upper surface of the piezoelectric substrate 23. Note that, in FIG. 5, the space 29, second inflow port 31, and passage 11 are also indicated by two-dotted chain lines.

On the upper surface of the piezoelectric substrate 23, in a region contained in the space 29, a first IDT electrode 45, a second IDT electrode 47, and a short-circuiting electrode 51 are formed.

The first IDT electrode 45 is for generating a predetermined SAW, while the second IDT electrode 47 is for receiving the SAW generated at the first IDT electrode 45. The second IDT electrode 47 is arranged on the path of propagation of the SAW which is generated in the first IDT electrode 45 so that the second IDT electrode 47 can receive the SAW generated in the first IDT electrode 45.

Each of the first IDT electrode 45 and second IDT electrode 47 has a pair of comb-shaped electrodes. Each comb-shaped electrode has a bus bar and a plurality of electrode fingers extending from the bus bar. Further, the pair of comb-shaped electrodes are arranged so that their plurality of electrode fingers mesh with each other. The first IDT electrode 45 and second IDT electrode 47 constitute a transversal type IDT electrode.

Using the numbers of electrode fingers of the first IDT electrode 45 and second IDT electrode 47, distance between adjacent electrode fingers, intersection width of electrode fingers, and so on as parameters, a frequency characteristic can be set. As the SAW excited by the IDT electrode, a Rayleigh wave, Love wave, Leaky wave, and so on exist. Any of them may be utilized. The sensor chip 9 for example utilizes a Love wave.

An elastic member for suppressing reflection of the SAW may be provided in a region on the outside of the first IDT electrode 45 and the second IDT electrode 47 in the propagation direction of the SAW as well. The frequency of the SAW can be set within a range of for example several megahertz (MHz) to several gigahertz (GHz). In particular, several hundred MHz to 2 GHz is practical, and the frequency can induce reduction of size of the piezoelectric substrate 23, consequently reduction of size of the sensor chip 9.

The first IDT electrode 45 and the second IDT electrode 47 are connected to the pads 27 through the wirings 49. Through these pads 27 and wirings 49, electric signals are input to the first IDT electrode 45, while electric signals are output from the second IDT electrode 47.

The short-circuiting electrode 51 is arranged in the region between the first IDT electrode 45 and the second IDT electrode 47 in the upper surface of the piezoelectric substrate 23, defined as the "detection region 23A". This short-circuiting electrode 51 is for electrically short-circuiting the portion which becomes the path of propagation of the SAW in the upper surface of the piezoelectric substrate 23. By providing this short-circuiting electrode 51, depending on the type of the SAW, the loss of the SAW can be made smaller. Note that, it is considered that the effect of suppression of loss by the short-circuiting electrode 51 is high particularly when a leaky wave is used as the SAW.

The short-circuiting electrode 51 is given for example a rectangular shape which extends along the path of propagation of the SAW which runs from the first IDT electrode 45 to the second IDT electrode 47. The width of the short-circuiting electrode 51 in a direction (x-direction) perpendicular to the propagation direction of the SAW is for example the same as the intersection width of the electrode fingers of the first IDT electrode 45. Further, the end part of the short-circuiting electrode 51 on the first IDT electrode 45 side in a direction (y-direction) parallel to the propagation direction of the SAW is located at a place which is separated from the center of the electrode finger which is located at the end part of the first IDT electrode 45 by exactly the amount of a half-wave length of the SAW. In the same way, the end part of the short-circuiting electrode 51 on the second IDT electrode 47 side in the y-direction is located at a place which is separated from the center of the electrode finger which is located at the end part of the second IDT electrode 47 by exactly the amount of a half-wave length of the SAW.

The short-circuiting electrode 51 may be placed in an electrically floating state, or a pad 27 for ground potential may be provided and the short-circuiting electrode 51 may be connected to this and made a ground potential. When the short-circuiting electrode 51 is made the ground potential, propagation of direct waves due to electromagnetic coupling between the first IDT electrode 45 and the second IDT electrode 47 can be suppressed.

The first IDT electrode 45, second IDT electrode 47, short-circuiting electrode 51, wirings 49, and pads 27 are for example made of gold, aluminum, an alloy of aluminum and copper, or the like. Further, these electrodes may be given a multilayer structure as well. When a multilayer structure is given, for example, the first layer may be made of titanium or chromium, the second layer may be made of aluminum, an aluminum alloy, or gold, and further titanium or chromium may be laminated as the uppermost layer.

Figure 6A:
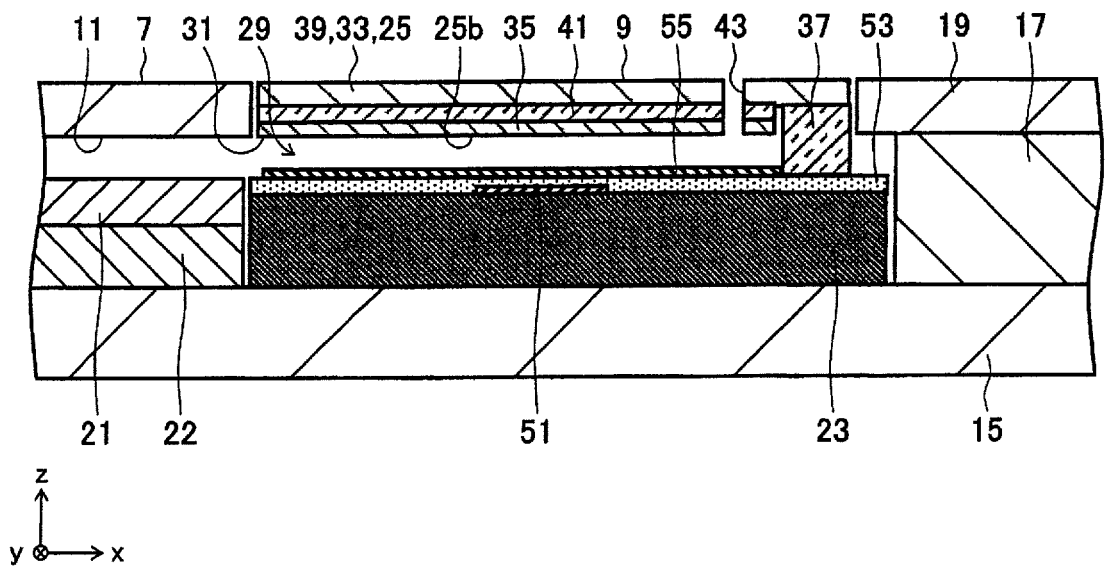
FIG. 6A is a cross-sectional view taken along a VIa-VIa line in FIG. 1.
Figure 6B:
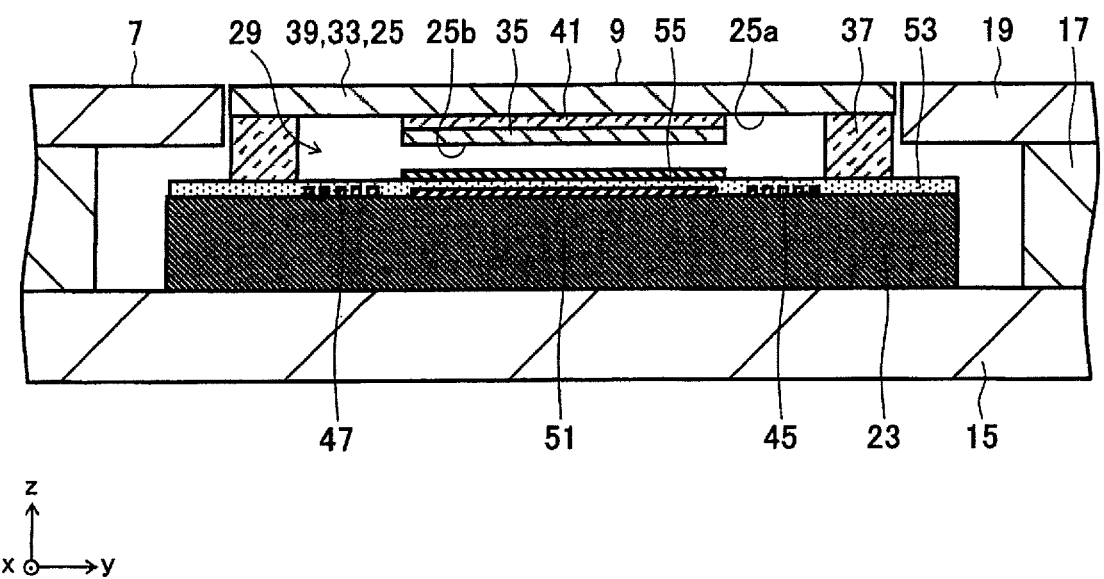
FIG. 6B is a cross-sectional view taken along a VIb-VIb line in FIG. 1.

FIG. 6A is a cross-sectional view taken along a VIa-VIa line in FIG. 1, while FIG. 6B is a cross-sectional view taken along a VIb-VIb line in FIG. 1.

On the upper surface of the piezoelectric substrate 23, a protective film 53, and a metal film 55 which is located on the protective film 53 are provided.

The protective film 53 covers the first IDT electrode 45, second IDT electrode 47, short-circuiting electrode 51, and wirings 49 and contributes to prevention of oxidation of these electrodes and wirings. The protective film 53 is made of for example an inorganic insulating material. The inorganic insulating material is for example silicon oxide, aluminum oxide, zinc oxide, titanium oxide, silicon nitride, or silicon. In the SAW sensor 1, use is made of silicon oxide ($SiO_2$) as the protective film 53.

The protective film 53 is formed over the entire upper surface of the piezoelectric substrate 23 but exposes the pads 27. The thickness of the protective film 53 (the height from the upper surface of the piezoelectric substrate 23) is for example thicker than the thickness of the first IDT electrode 45 and second IDT electrode 47. Further, the thickness of the protective film 53 is for example 200 nm to 10 µm. Note that, it is not always necessary to form the protective film 53 across the entire upper surface of the piezoelectric substrate 23. For example, the protective film 53 may be formed to coat only the vicinity of the center of the upper surface of the piezoelectric substrate 23 so that the region along the periphery of the upper surface of the piezoelectric substrate 23 including the pads 27 is exposed.

The metal film 55 is located between the first IDT electrode 45 and the second IDT electrode 47 on the protective film 53. Further, the metal film 55 for example spreads from the second inflow port 31 toward the deepest part of the space 29. The metal film 55 has for example a two-layer structure of chromium and gold which is formed on the chromium. On the surface of the metal film 55, for example aptamers made of nucleic acids or peptides are fixed.

When the liquid sample contacts the metal film 55 to which the aptamers are fixed, a specific target substance (detection object) in the liquid sample combines with the aptamers corresponding to that target substance and the weight of the metal film 55 changes. As a result, a phase characteristic etc. of the SAW which is propagated from the first IDT electrode 45 to the second IDT electrode 47 change. Accordingly, based on the change of the phase characteristic etc., the property or ingredients of the liquid sample can be checked. Note that, the protective film 53 can contribute to also improvement of measurement accuracy of the liquid sample by shifting the center of propagation of SAW from the vicinity of the upper surface of the piezoelectric substrate 23 to the upper part thereof.

Here, when the liquid sample flows up to the top of the first IDT electrode 45 and second IDT electrode 47, an inconvenience such as a drop of the detection sensitivity of the SAW sensor 1 and so on is liable to occur. Therefore, provision of a partition wall on the piezoelectric substrate 23 so as to partition the space 29 between the metal film 55 and each of the IDT electrodes may be considered. In this case, however, an inconvenience occurs such as propagation loss of the SAW and so on due to the partition wall when the SAW is propagated between the IDT electrodes and the metal film 55. Therefore, in the present embodiment, the flow of the liquid sample is restricted by the film 35. As a result, the flow of the liquid sample onto the IDT electrodes is suppressed without providing the partition wall. Specifically, this is as follows.

As shown in FIG. 5 and FIG. 6, the film 35 is set with the width (y-direction) thereof smaller than the width of the space 29, and faces the metal film 55 but does not face the first IDT electrode 45 and second IDT electrode 47. The first IDT electrode 45 and second IDT electrode 47 are faced by portions of the cover body 33 which are exposed from the film 35. Further, as already explained, the film 35 (strictly speaking, the main surface thereof) has a smaller contact angle to the liquid sample than the cover body 33.

In other words, the cover 25, on its lower surface, has second regions (as an example, electrode-facing surfaces 25A (FIG. 6B)) facing the first IDT electrode 45 and the second IDT electrode 47 and a first region (as an example, a detection part-facing surface 25B (FIG. 6A and FIG. 6B)) facing the detection part (detection region 23A) and having a smaller contact angle to the liquid sample than the electrode-facing surface 25A.

Accordingly, it becomes easier to guide the liquid sample to the top of the detection region 23A than the top of the IDT electrodes. As a result, flow of the liquid sample on the IDT electrodes can be suppressed without providing a partition wall between the IDT electrodes and the metal film 55.

From the viewpoint of suitably obtaining this action, a difference of contact angle to the liquid sample between the detection part-facing surface 25B and the electrode-facing surfaces 25A is preferably a certain degree of magnitude. For example, the difference of contact angle to the liquid sample is preferably 20° or more and further preferably 40° or more.

Further, in order to supply the liquid sample sufficiently with the metal film 55 in the y-direction, preferably the film 35 covers the entire metal film 55 in the y-direction and is not overlapped with the first IDT electrode 45 and second IDT electrode 47. That is, the width of the film 35 (y-direction) is preferably at least the width of the metal film 55 (y-direction) and preferably less than the distance between the first IDT electrode 45 and the second IDT electrode 47. Note that, the width of the film 35 is for example constant over the flow direction (x-direction).

Further, the film 35, in the x-direction, preferably extends from the second inflow port 31 (more preferably the edge on the second inflow port 31 side of the lid 39) to the position beyond the detection region 23a. In this case, the liquid sample which arrives at the second inflow port 31 from the passage 11 can be suitably guided to the top of the detection region 23A. Further, preferably the through hole 43 is formed at a position beyond the detection region 23A so that the air can be suitably discharged until the liquid sample goes beyond the detection region 23A.

The film 35 is adhered to the lower surface of the cover body 33 which is formed in a flat planar shape, therefore a step is formed with respect to the lower surface of the cover body 33 due to the thickness of the film 35 and adhesive agent 41. The height of the step is for example 1/2 to 3/2 of the distance between the film 35 and the metal film 55 or for example 50 µm to 300 µm. Further, the film 35 is for example formed by cutting a film having a main surface subjected to hydrophilization. Its cut cross-section (side surface) has a lower hydrophilicity compared with the main surface (lower surface), that is, has a larger contact angle to the liquid sample.

Accordingly, the liquid sample wetting the film 35 has a low possibility that passes beyond the side surfaces of the film 35 and wet the cover body 33 (electrode-facing surfaces 25A). As a result, for example, even if the hydrophilicity of the cover body 33 is not set lower so much, the possibility of the liquid sample spreading onto the IDT electrodes reduces, and consequently the selection of the materials of the cover body 33 grows.

In FIG. 5 and FIG. 6, the positional relationships of the passage 11 and space 29 etc. are exemplified. As shown in FIG. 5, the width of the passage 11 (y-direction) is preferably not more than the width of the film 35 (y-direction). In this case, the amount of the liquid sample in the space 29 which is provided for measurement can be made larger while reducing the total amount of the liquid sample. For example, when the width of the film 35 is about 3 mm, the width of the passage 11 is preferably 50 µm to 3 mm, more preferably 50 µm to 1 mm, furthermore preferably about 50 µm.

As shown in FIG. 6A, the ceiling surface of the passage 11 (lower surface of the upper layer member 19) is adjacent to the detection part-facing surface 25B (lower surface of the film 35) in the plane direction. Accordingly, the liquid sample can be expected to smoothly flow from the passage 11 to the space 29. Note that, preferably the ceiling surface of the passage 11 and the detection part-facing surface 25B are substantially flush. Adjustment for making them flush is possible by for example adjusting the thickness of the adhesive agent 41. The ceiling surface of the passage 11 may be substantially flush with the lower surface of the cover body 33 in a case where the thicknesses of the film 35 and adhesive agent 41 can be ignored.

Note that, when referring to "flush" or "in the same plane", this shall be deemed to include a case where two planes are not continuous (two planes are adjacent to each other through a gap) like with the relationship between the ceiling surface of the passage 11 and the detection part-facing surface 25B described above.

As shown in FIG. 6A, the bottom surface of the passage 11 (upper surface of the bottom surface member 21) is adjacent to the upper surface of the metal film 55 in the plane direction. Accordingly, the liquid sample is expected to smoothly flow from the passage 11 to the space 29. Note that, preferably the bottom surface of the passage 11 and the upper surface of the metal film 55 are substantially flush. Adjustment for making them flush is possible by for example adjusting the thickness of the adhesive agent 22. The bottom surface of the passage 11 may be substantially flush with the upper surface of the protective film 53 in a case where the thicknesses of the metal film 55 can be ignored.

The ceiling surface and bottom surface of the passage 11 are comprised of hydrophilic films, therefore their contact angles to the liquid sample are smaller than those at the electrode-facing surfaces 25A (cover body 33) in the ceiling surface of the space 29. Accordingly, in the SAW sensor 11, the liquid sample can be suitably guided to the space 29 in the passage 11, while wetting of the electrode-facing surfaces 25A by the liquid sample is suppressed. Either of the contact angles to the liquid sample at the ceiling surface and bottom surface of the passage 11 and the contact angle to the liquid sample at the detection part-facing surface 25B (film 35) in the ceiling surface of the space 29 may be higher or they may be the same degree.

FIG. 7A to FIG. 7D are cross-sectional views for explaining the method of manufacturing the sensor chip 9. The manufacturing process advances in order from FIG. 7A to FIG. 7D.

Figure 7A:
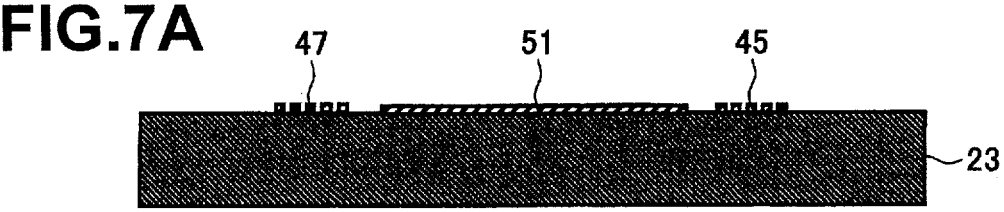
FIG. 7A to FIG. 7D are cross-sectional views for explaining a method for manufacturing the sensor chip in FIG. 3.

First, as shown in FIG. 7A, on the upper surface of the piezoelectric substrate 23, the first IDT electrode 45, second IDT electrode 47, short-circuiting electrode 51, wirings 49, and pads 27 etc. are formed. Specifically, first, by a sputtering method, vapor deposition process, CVD (chemical vapor deposition) process, or other thin film forming method, a metal layer is formed on the upper surface of the piezoelectric substrate 23. Next, the metal layer is patterned by a photolithography process using a reduced projection exposure apparatus (stepper) and a RIE (reactive ion etching) apparatus. By patterning the metal layer, all kinds of electrodes, wirings, etc. are formed.

Figure 7B:
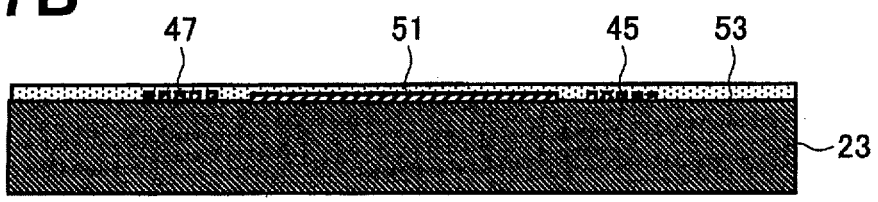

After the first IDT electrode 45 etc. are formed, the protective film 53 is formed as shown in FIG. 7B. Specifically, first, a thin film which becomes the protective film 53 is formed. The thin film forming method is for example the sputtering method or CVD process. Next, a portion of the thin film is removed by RIE or the like so that the pads 27 are exposed. Due to this, the protective film 53 is formed.

Figure 7C:
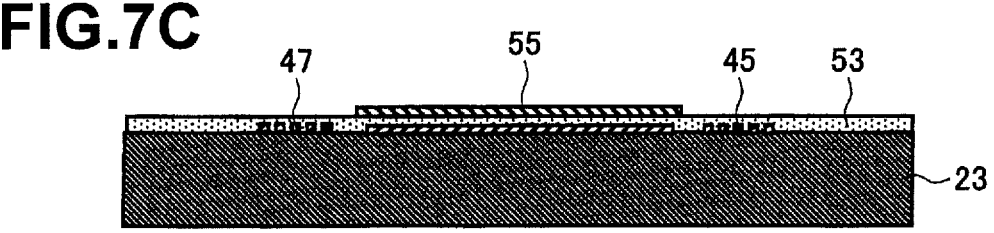

After the protective layer 53 is formed, the metal film 55 is formed as shown in FIG. 7C. Specifically, by the vapor deposition process or sputtering process or the like, a metal material is formed on the protective film 53 through a mask which is not shown and has an opening given the same shape as that of the metal film 55. After that, aptamers are arranged on the metal film 55. Alternatively, aptamers may be fixed onto the metal film 55 by chemical bonding or the like.

Figure 7D:
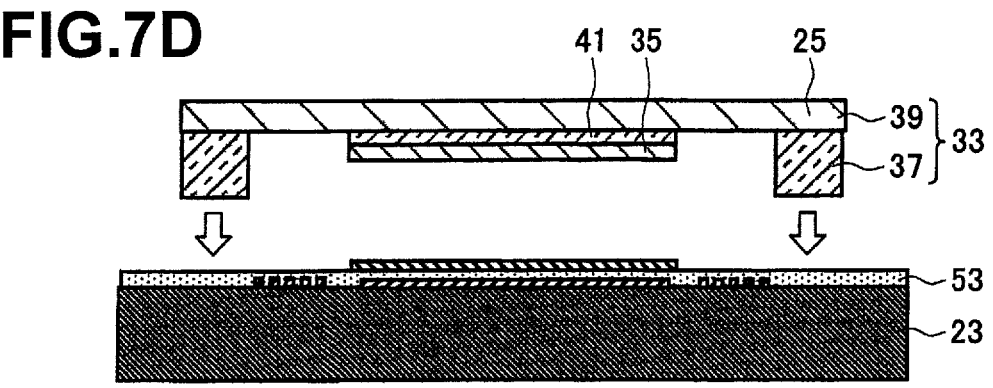

Finally, as shown in FIG. 7D, the cover 25 is attached to the piezoelectric substrate 23. Specifically, first, a fluid material made of polydimethylsiloxane or the like is poured into a predetermined mold, then this is hardened to thereby form the cover body 33. Note that, in this method of formation, the frame 37 and the lid 39 are integrally formed. Next, the film 35 is adhered to the lid 39 by the adhesive agent 41. After that, in the cover body 33, at least a portion which will contact the protective film 53 is subjected to an oxygen plasma treatment, the cover body 33 is brought into contact with the protective film 53, and the cover body 33 is joined with the piezoelectric substrate 23.

Note that, in this way, in the case where an oxygen plasma treatment is applied to the cover body 33 made of polydimethylsiloxane and the cover body 33 is brought into contact with the protective film 53 made of SiO2, the cover body 33 and the protective film 53 can be bonded without use of an adhesive agent or the like. The reason for this is not always apparent, but it is considered that they can be bonded by formation of a covalent bond of Si and O between the cover body 33 and the protective film 53. Note, the cover body 33 may be bonded to the protective film 53 by using an adhesive agent as well.

The sensor chip 9 formed as described above is then held in the base 7. For example, first, the sensor chip 9 is fixed to the lower layer member 15 by an adhesive agent and electrically connected with the wirings 13 by wire bonding. After that, the middle layer member 17 and the upper layer member 19 are adhered to the lower layer member 15, resulting in that the sensor chip 9 being held in the base 7.

As described above, in the present embodiment, the SAW sensor 1 has the piezoelectric substrate 23, the first IDT electrode 45 and second IDT electrode 47 which are located on the upper surface of the piezoelectric substrate 23 and are separated from each other while sandwiching the detection part (detection region 23A) on the piezoelectric substrate 23 there between, and the cover 25 which forms the space 29 being on the first IDT electrode 45, second IDT electrode 47, and detection part and straddling them. On the lower surface of the cover 25, the detection part-facing surface 25B (lower surface of the film 35) facing the detection part has a smaller contact angle to the liquid sample than that of a pair of electrode-facing surfaces 25A (lower surface of the cover body 33) facing the first IDT electrode 45 and second IDT electrode 47.

Accordingly, as already explained, the width of the liquid sample (y-direction) in the space 29 can be controlled according to the width of the detection part-facing surface 25B (y-direction). As a result, for example, it is not necessary to provide a partition wall between the IDT electrodes and the detection part for preventing the liquid sample from flowing onto the IDT electrodes.

Since a partition wall is not provided, the propagation loss of the SAW is reduced, and an SN ratio is improved. For example, when a partition wall is formed by an epoxy resin, the width of the partition wall can be made thin down to about 25 µm. However, even in a case where the width is made thin down to that, occurrence of a propagation loss of about 5 dB is confirmed. On the other hand, according to the SAW sensor 1, since there is no partition wall, the propagation loss can be improved by 5 dB or more compared with the case where the partition wall is formed by an epoxy resin. Further, there also exists the advantage that the shape of the frame 37 for forming the partition wall is simplified. As a result, in a case where the frame 37 and the lid 39 are separately formed, bonding of them is facilitated. For example, the adhesive agent used for bonding is less liable to be exuded to the top of the detection region 23A. Further, since the liquid sample does not contact the partition wall, there is no necessity of applying treatment to the partition wall in order to suppress nonspecific absorption. Since there is no need to secure an area large enough to arrange the partition wall between the metal film 55 and the IDT electrodes either, it is possible to make the distance between the metal film 55 and the IDT electrodes shorter, and facilitate improvement of the detection accuracy as well.

Further, the thickness of the liquid sample is defined according to the height of the space 29 (distance between the metal film 55 and the film 35), while the width of the liquid sample is defined according to the width of the film 35. Therefore, it is possible to keep the mass of the liquid sample in the detection region 23A constant, and suppress measurement error due to variation of mass of the liquid sample as well.

Note that, the SAW sensor 1 may be one allowing the liquid sample to flow onto the IDT electrodes as well. Even in this case, various effects are exhibited because the detection part-facing surface 25B (first region) has a smaller contact angle to the liquid sample than those at the electrode-facing surfaces 25A (pair of second regions which are positioned at the two sides of the detection part-facing surface 25B in the direction of alignment (y-direction) of the detection part and the IDT electrodes).

For example, if the contact angles to the liquid sample are equal between the detection part-facing surface 25B and the electrode-facing surfaces 25A, by flow of the liquid sample along the inner wall of the passage 11 or space 29, the liquid sample flows onto the IDT electrodes prior to the top of the detection part-facing surface 25B. As a result, air bubbles are liable to form on the detection part. However, by making the contact angle to the liquid sample at the detection part-facing surface 25B smaller than those at the electrode-facing surfaces 25A and making the liquid sample flow onto the detection part with a higher priority, formation of such air bubbles is suppressed.

Second Embodiment

Figure 8:
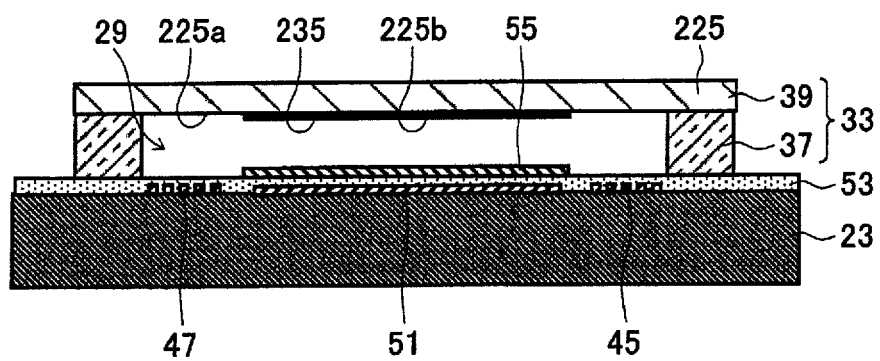
FIG. 8 is a cross-sectional view showing a sensor chip of a SAW sensor according to a second embodiment.

FIG. 8 is a cross-sectional view showing a sensor chip 209 of a SAW sensor according to a second embodiment. Note that, the cross-sectional view corresponds to a portion of FIG. 6B.

The sensor chip 209 differs from the sensor chip 9 in the first embodiment only in the point that a coating layer 235 is provided in place of the film 35 and adhesive agent 41. That is, in the sensor chip 209, at the lower surface of a cover 225, electrode-facing surfaces 225A facing the first IDT electrode 45 and the second IDT electrode 47 are constituted by surfaces of the cover body 33 (base material) on which the coating layer 235 is not arranged, and a detection part-facing surface 225B facing the detection part (detection region 23A) is constituted by a surface of the cover body 33 on which the coating layer 235 is arranged.

The coating layer 235 is formed by applying a hydrophilization treatment to the cover body 33 (base material). For example, in the cover body 33, in the region which becomes the detection part-facing surface 25B, ashing is performed by oxygen plasma, a silane coupling agent is coated, and finally polyethylene glycol is coated. Note that in this case, the coating layer 235 is constituted by polyethylene glycol. Other than this, it may be surface treated by using a treatment agent having phosphorylcholine to form a coating layer 235 made of phosphorylcholine as well.

The coating layer 235 is made of a material having a higher hydrophilicity than the material for the cover body 33. Accordingly, on the surface of the cover body 33 on which the coating layer 235 is arranged, the wettability with respect to the liquid sample becomes higher (that is, the contact ability with the liquid sample is smaller) than that on the surface on which it is not arranged.

The coating layer 235 is preferably arranged (superimposed) on the cover body 33 to an extent forming a layer state. The thickness thereof is thin compared with the total thickness of the film 35 and adhesive agent 41 in the first embodiment. For example, it is 5 A to 50 nm. Note that, the thickness of the frame 37 (height of the space 29 on the IDT electrodes) may be the same as that in the first embodiment or may be made thinner than the latter by the amount of reduction of thickness which is achieved by making the coating layer thinner than the film 35 and adhesive agent 41.

As described above, in the present embodiment, in the same way as the first embodiment, on the lower surface of the cover 25 which forms the space 29 on the first IDT electrode 45, second IDT electrode 47, and detection part so as to straddle them, the detection part-facing surface 225B facing the detection part has a smaller contact angle to the liquid sample than that of the pair of electrode-facing surfaces 225A facing the pair of IDT electrodes.

Accordingly, in the present embodiment as well, the same effects as those by the first embodiment are exhibited. For example, it is possible to control the width of the liquid sample (y-direction) in the space 29 according to the width (y-direction) of the detection part-facing surface 225B, and flow of the liquid sample onto the IDT electrodes can be suppressed without providing a partition wall.

Further, in the present embodiment, compared with the first embodiment, for example, the coating layer is thin as explained above, therefore a thinner sensor chip 209 can be achieved. Note that, in the first embodiment, compared with the present embodiment, for example, simplification of the manufacturing process and reduction of cost can be expected, further, as already explained, due to the low wettability step which is formed by the film 35, the effect of suppression of flow of the liquid sample onto the IDT electrodes can be expected.

Third Embodiment

Figure 9:
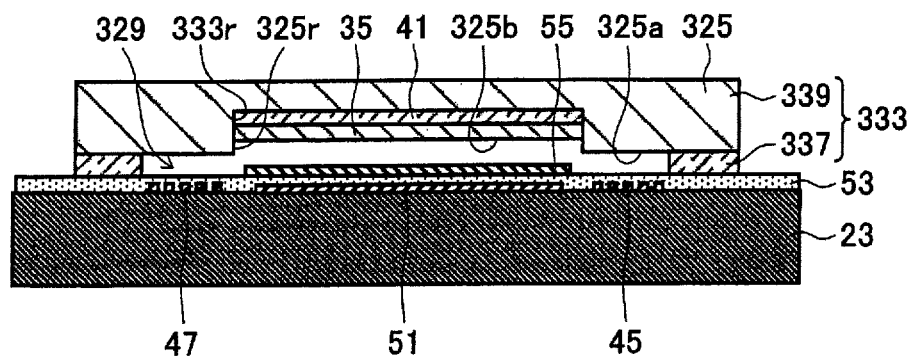
FIG. 9 is a cross-sectional view showing a sensor chip of a SAW sensor according to a third embodiment.

FIG. 9 is a cross-sectional view showing a sensor chip 309 of a SAW sensor according to a third embodiment. Note that, the cross-sectional view corresponds to a portion in FIG. 6B.

The sensor chip 309 differs from the sensor chip 9 in the first embodiment only in the point that a first groove 325R is formed by electrode-facing surfaces 325A facing IDT electrodes projecting to the piezoelectric substrate 23 side more than a detection part-facing surface 325B facing the detection part.

Specifically, on the lower surface of a lid 339 of a cover body 333, a second groove 333R deeper than the total thickness of the film 35 and adhesive agent 41 is formed. By accommodation of the adhesive agent 41 and film 35 in this second groove 333r, the first groove 325r defining the lower surface of the film 35 as its bottom surface is constituted.

The width and length of the second groove 333r are for example equal to the width and length of the film 35. In the same way as the first embodiment, the film 35 preferably extends up to the edge on the passage 11 (see FIG. 1) side of the lid 339, and consequently preferably the second groove 333r (first groove 325r) also extends up to the edge. Note, the second groove 333r may be longer than the film 35 and a bit broader.

An interval between the detection part-facing surface 325b (film 35) and the metal film 55 (thickness of liquid sample) is for example the same as that in the first embodiment. From another viewpoint, the frame 337 in the present embodiment is thinner than the frame 37 in the first embodiment, and the interval between the electrode-facing surfaces 325a and the protective film 53 in the present embodiment is smaller than the interval between the electrode-facing surfaces 25a and the protective film 53 in the first embodiment.

As described above, in the present embodiment, in the same way as the first embodiment, on the lower surface of the cover 325 which forms the space 29 on the first IDT electrode 45, second IDT electrode 47, and detection part so as to straddle them, the detection part-facing surface 325b facing the detection part has a smaller contact angle to the liquid sample than the pair of electrode-facing surfaces 325a facing the pair of IDT electrodes.

Accordingly, in the present embodiment as well, the same effects as those by the first and second embodiments are exhibited. For example, the width of the liquid sample (y-direction) in the space 329 can be controlled according to the width of the detection part-facing surface 325b (y-direction), and flow of the liquid sample onto the IDT electrodes can be suppressed without providing a partition wall.

Further, the liquid sample between the detection part-facing surface 325b and the metal film 55 contacts the side surfaces of the first groove 325r at its side surfaces. Accordingly, the liquid sample is reduced in area contacting the gas (for example air) surrounding the SAW sensor. As a result, evaporation of the liquid sample is suppressed, therefore the required amount of the liquid sample can be suppressed.

Note that, in the present embodiment, in the same way as the first embodiment, the detection part-facing surface 325b was constituted by the film 35. However, the detection part-facing surface 325b may be constituted by a coating layer in the same way as the second embodiment as well. In this case, the coating layer may be provided on only the bottom surface of the first groove 325r (second groove 333r) or may be provided on the side surfaces in addition to the bottom surface.

Fourth Embodiment

Figure 10:
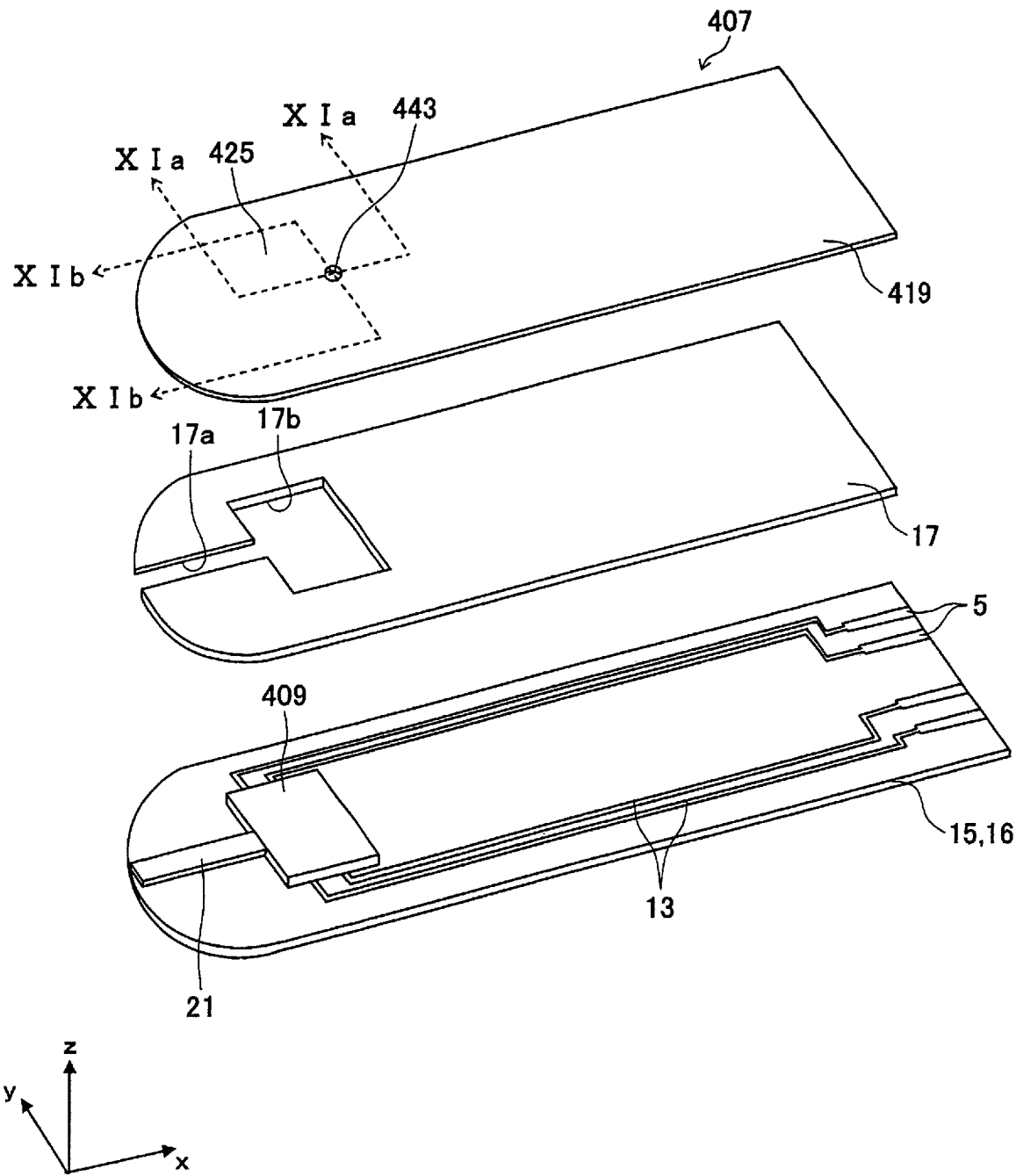
FIG. 10 is a disassembled perspective view showing a SAW sensor according to a fourth embodiment of the present invention.
Figure 11A:
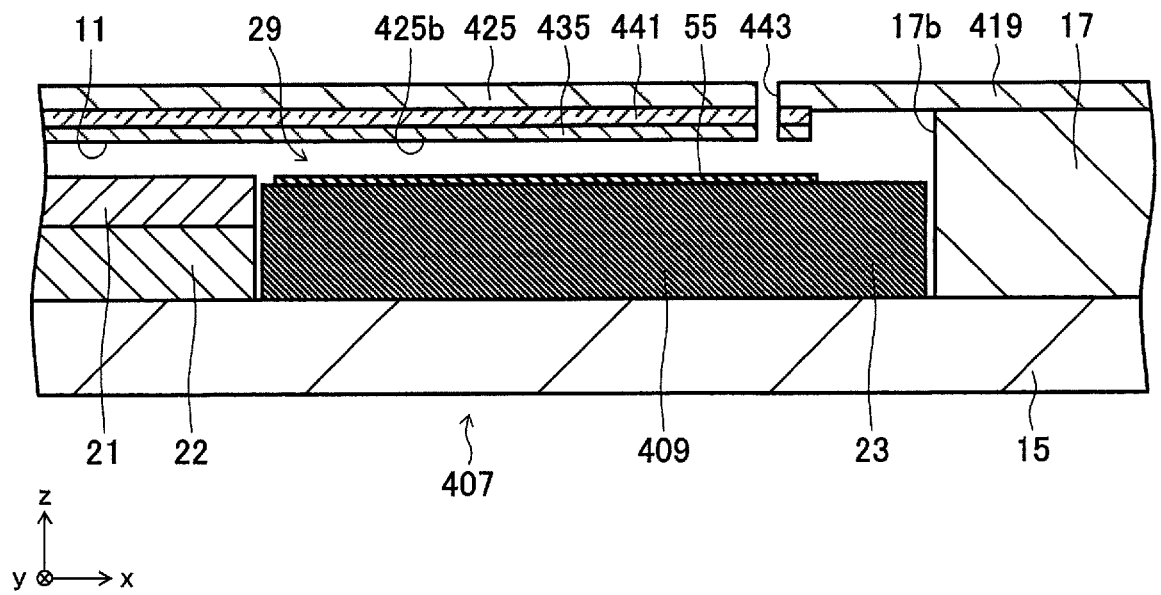
FIG. 11A is a cross-sectional view taken along an XIa-XIa line in FIG. 10.
Figure 11B:
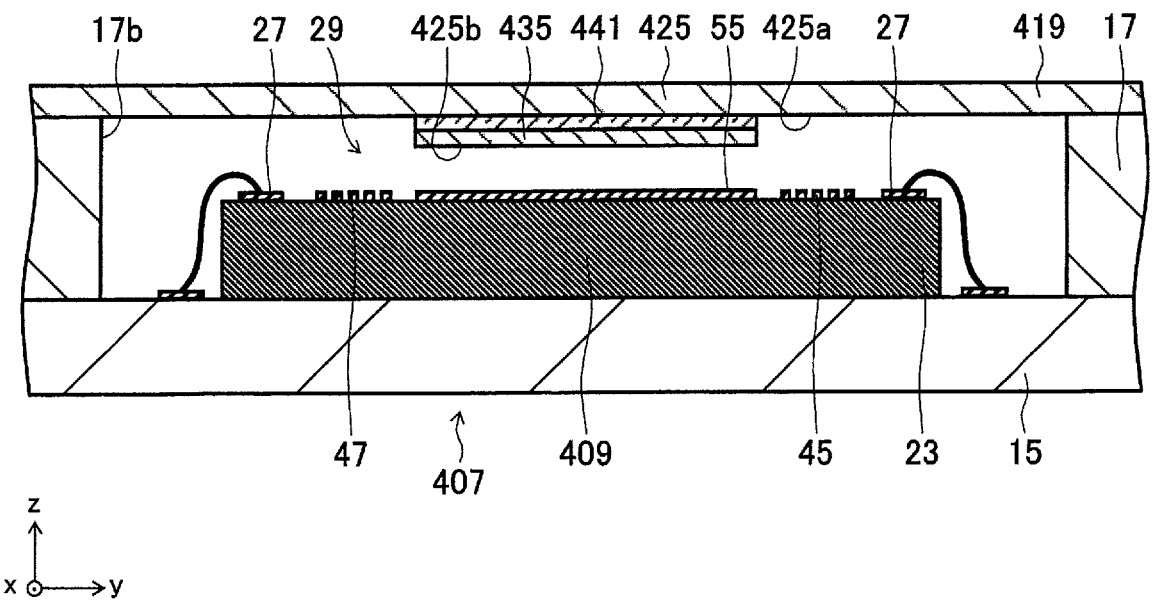
FIG. 11B is a cross-sectional view taken along an XIb-XIb line in FIG. 10.

FIG. 10 is a disassembled perspective view showing a SAW sensor 401 according to a fourth embodiment. FIG. 11A is a cross-sectional view taken along an XIa-XIa line in FIG. 10, while FIG. 11B is a cross-sectional view taken along an XIb-XIb line in FIG. 10.

In the first embodiment, the sensor chip 9 had the cover 25. Contrary to this, the sensor chip 409 in the fourth embodiment does not have a cover 25. Further, in the SAW sensor 401 in the fourth embodiment, the middle layer member 17 and an upper layer member 419 constitute a cover 425. Specifically, this is as follows.

The sensor chip 409 has roughly a constitution achieved by eliminating the cover 25 from the sensor chip 9. That is, as shown in FIG. 11, the sensor chip 409, in the same way as the sensor chip 9, has the piezoelectric substrate 23, and has the first IDT electrode 45, second IDT electrode 47, wirings 49, pads 27, and metal film 55 etc. on the piezoelectric substrate 23.

Note, in the fourth embodiment, the piezoelectric substrate 23 does not need space for arranging the cover 25, therefore may be made smaller in size than the piezoelectric substrate 23 in the first embodiment. The first hole part 17b in the middle layer member 17 may be made smaller in accordance with this.

In the sensor chip 409, the short-circuiting electrode 51 and protective film 53 are omitted. However, the sensor chip 409 may have the short-circuiting electrode 51 and protective film 53 in the same way as the sensor chip 9 as well.

The SAW sensor 401, in the same way as the SAW sensor 101, has a base 407 constituted by stacking the lower layer member 15, middle layer member 17, and upper layer member 419. The constitutions of the lower layer member 15 and middle layer members 17 are roughly the same as those in the first embodiment.

In the upper layer member 419, unlike the first embodiment, the second hole part 19b (FIG. 1) is not formed. Accordingly, in the upper layer member 419, a portion superimposed on the first hole part 17b in the middle layer member 17 covers the upper surface of the sensor chip 409 (piezoelectric substrate 23). In this way, the cover 425 is constituted by the middle layer member 17 and the upper layer member 419. Note that, only the upper layer member 419 may be regarded as the member constituting the cover as well.

The cover 425, in the same way as the cover 25 in the first embodiment, has a cover body 433 and a film 435 which is adhered to the lower surface of the cover body 433 by an adhesive agent 441. Further, in the cover 425, a through hole 443 for exhaust is formed.

The ceiling portion of the cover body 433 (upper layer member 419) is for example formed by a hydrophilic film in the same way as the upper layer member 19 in the first embodiment. Further, the film 435 is constituted by a hydrophilic film having a higher hydrophilicity than the cover body 433. Note that, the upper layer member 419 may be constituted by a material having a relatively low wettability (for example the same material as that for the lower layer member 15 and middle layer members 17) as well.

Further, the film 435 forms a detection part-facing surface 425b facing the detection part (metal film 55). The portions of the cover body 433 to which the film 435 is not adhered form electrode-facing surfaces 425a facing the first IDT electrode 45 and the second IDT electrode 47.

The film 435, in the x-direction, extends up to not only the range facing the piezoelectric substrate 23, but also the passage 11 for guiding the liquid sample to the space 29 on the piezoelectric substrate 23. Due to this, the detection part-facing surface 425b and the ceiling surface of the passage 11 are flush.

Note that, the thickness of the middle layer member 17 may be suitably set so that the heights of the space 29 and the passage 11 become suitable.

As described above, in the present embodiment, on the ceiling surface of the cover 425 constituting the space 29, the detection part-facing surface 425b facing the detection part has a smaller contact angle to the liquid sample than that at the pair of electrode-facing surfaces 425a facing the pair of IDT electrodes.

Accordingly, in the present embodiment as well, the same effects as those by the first embodiment are exhibited. For example, the width of the liquid sample in the space 29 (y-direction) can be controlled according to the width of the detection part-facing surface 426b (y-direction), and flow of the liquid sample onto the IDT electrodes can be suppressed without providing a partition wall.

Further, in the present embodiment, the cover 425 has the middle layer member 17 which is located on the lower layer member 15 and is located in the lateral direction of the piezoelectric substrate 23 and has the upper layer member 419 which is located on the middle layer member 17 and covers the upper surface of the piezoelectric substrate 23. Accordingly, for example, the configuration is simplified compared with the first embodiment.

Note that, in the present embodiment, in the same way as the first embodiment, the detection part-facing surface 425b was constituted by a film. However, in the same way as the second embodiment, the detection part-facing surface 425b may be constituted by a coating layer as well. In this case, the coating layer may be provided only on the detection part-facing surface 425b or may be provided also on the ceiling surface of the passage 11 in the same way as the film 435.

Fifth Embodiment

Figure 12A:
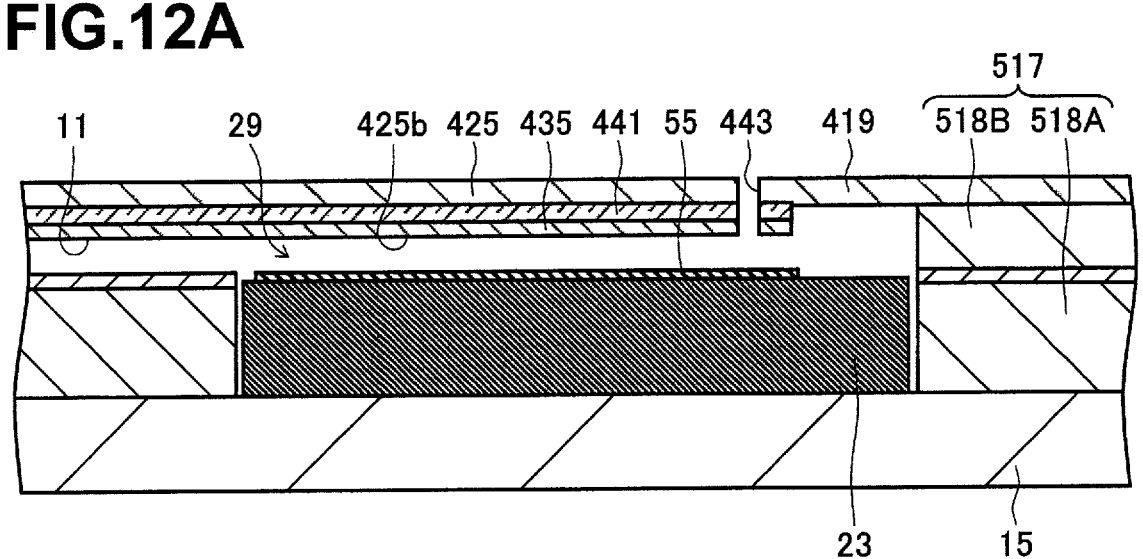
FIG. 12A and FIG. 12B are cross-sectional views showing a SAW sensor according to a fifth embodiment of the present invention.
Figure 12B:
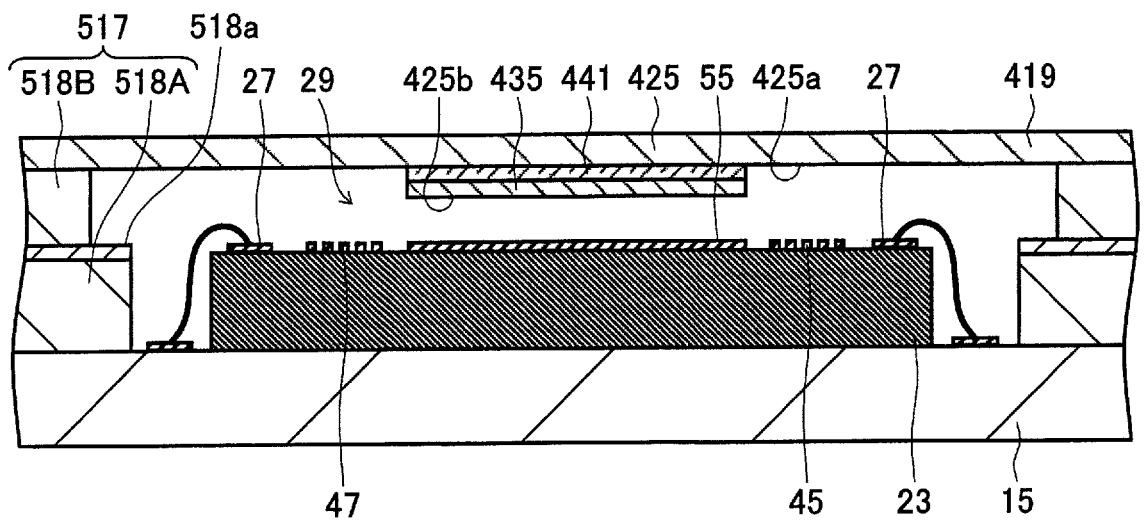

FIG. 12A and FIG. 12B are cross-sectional views showing a SAW sensor 501 according to a fifth embodiment and correspond to FIG. 11A and FIG. 11B.

The SAW sensor 501 is different from the SAW sensor 401 in the fourth embodiment only in the constitution of the middle layer member. Specifically, this is as follows.

The middle layer member 517 in the SAW sensor 501 has a first layer 518A located on the lower layer member 15 and a second layer 518B located on the former.

A planar shape of the second layer 518B is for example the same as the planar shape of the middle layer member 17 in the fourth embodiment.

The planar shape of the first layer 518A is for example made a shape where, in the planar shape of the second layer 518B, the hole part constituting the space 29 is made small in the y-direction (the direction of alignment of the detection part and IDT electrodes) and a cutout portion forming the passage 11 is eliminated.

Accordingly, as shown in FIG. 12B, in the y-direction, the first layer 518A is nearer the piezoelectric substrate 23 than the second layer 518B. Further, a portion (exposed surface 518a) of the upper surface of the first layer 518A is exposed in the space 29 from the second layer 518B.

Further, as shown in FIG. 12A, the upper surface of the first layer 518A is exposed from the cutout for forming the passage 11 in the second layer 518B and constitutes the bottom surface of the passage 11. Note that, in the present embodiment, the bottom surface member 21 which constituted the bottom surface of the passage 11 in the first embodiment is not provided.

The upper surface of the first layer 518A (at least the exposed surface from the second layer 518B) is constituted so that the contact angle to the liquid sample becomes relatively small. For example, the upper surface of the first layer 518A is constituted by a hydrophilic film or a coating layer is arranged on the upper surface of the first layer 518A, so the contact angle to the liquid sample is made small at the upper surface of the first layer 518A. The contact angle to the liquid sample at the upper surface of the first layer 518A is for example smaller than the contact angles to the liquid sample at the electrode-facing surfaces 425a and is larger than the contact angle to the liquid sample at the detection part-facing surface 415b.

As described above, in the present embodiment, the middle layer member 517 has the first layer 518A and second layer 518B, and the first layer 518A is nearer the piezoelectric substrate 23 than the second layer 518B in the y-direction.

Accordingly, for example, in a constitution predicated on the liquid sample being filled in the entire space 29, the amount of liquid sample can be reduced compared with the fourth embodiment.

Further, in the present embodiment, the exposed surface 518a which is a portion of the upper surface of the first layer 518A and is exposed from the second layer 518B by the first layer 518A being nearer the piezoelectric substrate 23 than the second layer 518B has a smaller contact angle to the liquid sample than the electrode-facing surfaces 425a and has a larger contact angle to the liquid sample than the detection part-facing surface 425b.

Accordingly, for example, in a constitution predicated on the liquid sample being filled in the entire space 29, the liquid sample can be easily filled in the entire space 29 while making the liquid sample flow to the detection part-facing surface 425b with a higher priority.

Sixth Embodiment

Figure 13:
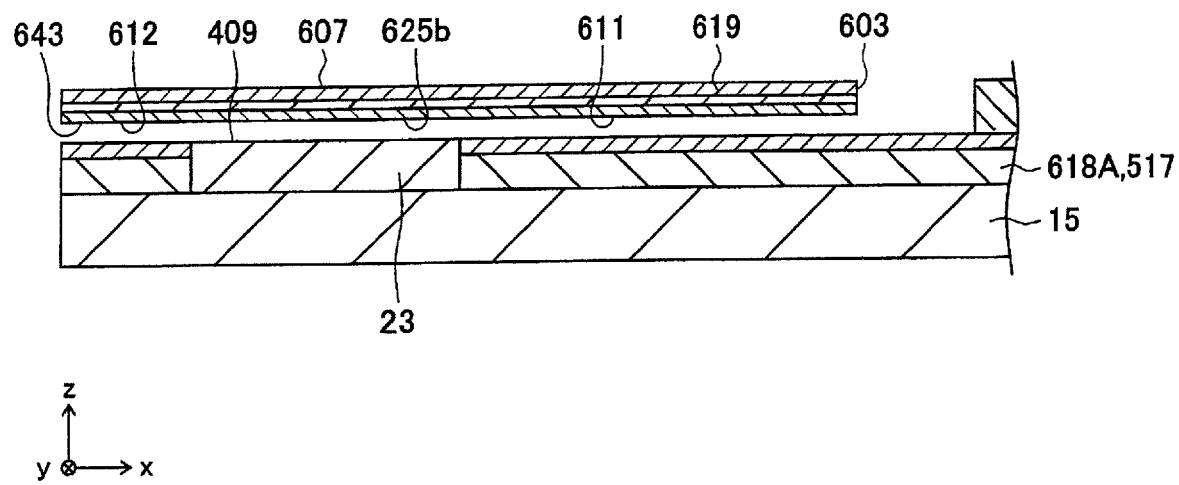
FIG. 13 is a cross-sectional view showing a SAW sensor according to a sixth embodiment of the present invention.

FIG. 13 is a cross-sectional view showing a SAW sensor 601 according to a sixth embodiment and corresponds to a portion in FIG. 12A.

In the first to fifth embodiments, the inflow port (3 etc.) was formed in the side surface of the base (7 etc.) and the through hole (43 etc.) for exhaust was formed in the upper surface of the base. In the sixth embodiment, conversely to this, an inflow port 603 is opened in the upper surface of a base 607, and a through hole 643 for exhaust is opened in the side surface of the base 607. Specifically, this is as follows.

In the SAW sensor 601, for example, in the same way as the fourth and fifth embodiments, the sensor chip 409 does not have a cover, and a cover covering the piezoelectric substrate 23 is constituted by an upper layer member 619. The inflow port 603 is formed in the upper layer member 619.

Further, in the SAW sensor 601, for example, in the same way as the fifth embodiment, a middle layer member 517 has a first layer 618A and a second layer (not shown), and a cutout for forming a passage etc. is formed in the second layer. Due to this, between the first layer 618A and the upper layer member 619, a space 29 above the sensor chip 409, a passage 611 for guiding the liquid sample to the space 29, and a passage 612 for exhaust from the space 29 are formed.

The inflow port 603 is opened in for example the upper surface of one end of the passage 611 for inflow. The passage 611 for example linearly extends from the inflow port 603 toward the space 29. The passage 612 for exhaust for example linearly extends to the side opposite to the passage 611 from the space 29 and is communicated with a through hole 643.

On the lower surface of the upper layer member 619, in the same way as the other embodiments, the contact angle to the liquid sample at the detection part-facing surface 625b becomes smaller than the contact angle to the liquid sample at the adjacent surface (second region, not shown). For example, in the same way as the fourth and fifth embodiments, on the lower surface of the upper layer member 619, a film 635 is provided so as to face the detection part.

Further, in the same way as the fifth embodiment, on the upper surface of the first layer 618A, due to the provision of the hydrophilic film or the like, the contact angle to the liquid sample becomes relatively small. That is, the contact angles to the liquid sample at the bottom surfaces of the passages 611 and 612 are small.

Note that, at the wall surface near the connection portion of the inflow port 603 and the passage 611 as well, preferably the contact angle to the liquid sample is set small due to the provision of a hydrophilic film or the like.

In the constitution as described above as well, effects the same as those by the first to fifth embodiments are exhibited. For example, the width of the liquid sample (y-direction) in the space 29 can be controlled according to the width of the detection part-facing surface 625b (y-direction), and flow of the liquid sample onto the IDT electrodes can be suppressed without providing a partition wall.

(Modification of Shape of Passage)

Figure 14:
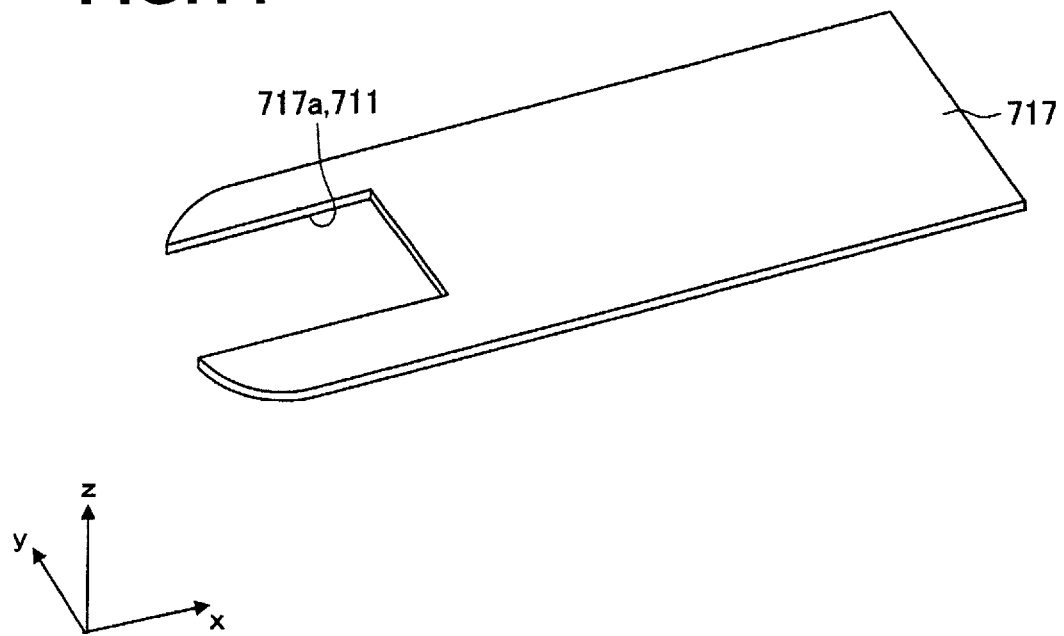
FIG. 14 is a perspective view for explaining a modification showing the shape of a passage

FIG. 14 is a view for explaining a modification of the shape of the passage which guides the liquid sample onto the detection part and is a perspective view of a middle layer member 717.

The middle layer member 717 is, in the same way as the middle layer members in the embodiments explained above, a member which are interposed between the lower layer member and the upper layer member. A passage 711 for guiding the liquid sample to the detection part is formed by formation of a cutout 717a in the middle layer member 717.

The cutout 717a extends with a constant width from the end part constituting the inflow port up to the position at which a sensor chip is arranged, and includes a portion which corresponds to the first hole part 17b in the first embodiment as well. Note that, in the passage 711, the width (range of y-direction) making the contact angle to the liquid sample small on the bottom surface or ceiling surface may be equal to the width of the cutout 717a or may be smaller than the width of the cutout 717a.

Note that, in the above embodiments, the detection part-facing surfaces 25b, 225b, 325b, 425b, and 625b are examples of the first region, the electrode-facing surfaces 25a, 225a, 325a, and 425a are examples of the second region, the bases 7, 407, and 607 are examples of the package, the lower layer member 15 is an example of the lower layer portion, the middle layer members 17 and 517 are examples of the middle layer portion, and the upper layer member 419 is an example of the upper layer portion.

The present invention is not limited to the above embodiments and may be executed in various ways.

In the embodiments, the case where the SAW sensor had a sensor chip and a base was exemplified, but the SAW sensor may be marketed in the form of only a sensor chip as a finished product.

Note, if configuring the SAW sensor having a sensor chip including a cover and a base, for example, the height of the space 29 and the width of the first region are formed with a high precision, variation of the amount of the liquid sample in the detection part is suppressed, and consequently the detection precision is improved, while the demand for precision can be lowered at the relatively large base 7. Therefore a cheap SAW sensor having a high detection precision can be realized.

Further, in the first embodiment etc., the cover 25 of the sensor chip 9 was exposed from the base 7. However, the base may be constituted so that the sensor chip 9 is not exposed to the outside as well. For example, the base may further have a layer-shaped member which is adhered to the tops of the upper layer member 19 and the cover 25 and has a through hole communicated with the through hole 43 formed therein as well.

Further, in the fourth embodiment, the middle layer member 17 was located in the four lateral directions of the sensor chip 409 and surrounded roughly the entire sensor chip 409. Further, in the modification of FIG. 4, the middle layer member 717 was located in the three lateral directions of the sensor chip. However, the middle layer member only has to be located on at least two sides of the sensor chip in a lateral direction. For example, an inflow path (see FIG. 14) which extends toward the space above the detection part and has a width equal to the width of the space and an outflow path (or exhaust path) which extends from the space to the side opposite to the inflow path and has a width equal to the width of the space may be formed as well.

The lower layer portion and middle layer portion may be integrally formed, and the upper layer member (upper layer portion) may be covered on that. In this case as well, the lower layer portion and the middle layer portion can be differentiated using the surface on which the piezoelectric substrate is placed as the standard. Further, the middle layer portion and the upper layer portion may be integrally formed, and they may be placed on the lower layer member (lower layer portion) as well. In this case as well, the middle layer portion and the upper layer portion can be differentiated using the upper surface of the space on the piezoelectric substrate as the standard.

Further, the passage in which the liquid sample flows (including not only the passage of the base, but also the space of the sensor chip) can be suitably constituted other than ones exemplified in the above embodiments.

Boundaries between the first region and the pair of second regions which are located on the two sides of the first region in the direction of alignment of the detection part and the IDT electrodes do not always have to be located between the detection part and the IDT electrodes. For example, the boundaries between the first region and the second regions may be located on the IDT electrodes or may be located on outer sides from the IDT electrodes. Even in such cases, for example, in an SAW sensor allowing the liquid sample to flow onto the IDT electrodes, it is possible to make the liquid sample flow onto the detection part with a higher priority, the formation of air bubbles on the detection part can be suppressed.

On the lower surface of the cover, the contact angle to the liquid sample in the first region only has to be smaller than the contact angle to the liquid sample in the second region. For example, in the first region, the contact angle to the liquid sample need not be less than 90°. For example, even in a case where the capillary phenomenon is not utilized, so long as the contact angle to the liquid sample in the first region is smaller than the contact angles to the liquid sample on the electrode-facing surfaces, the liquid sample can be made flow onto the detection part while suppressing flow of the liquid sample onto the IDT electrodes. However, the introduction of the liquid sample onto the detection part is easier in the case where the capillary phenomenon is utilized, and it is also easy to control the width (amount) of the liquid sample with a high precision according to the width of the first region etc.

Further, in the case where the contact angle to the liquid sample in the first region is less than 90°, the contact angle to the liquid sample in the second region need not be 90° or more. For example, in a trial piece of the SAW sensor 1 according to the first embodiment, the contact angles at the electrode-facing surfaces 25a were 70°, and the contact angle at the detection part-facing surface 25b was 25°. However, the flow of the liquid sample onto the IDT electrodes was sufficiently suppressed. The reason for this is considered to be the effect of the low wettability step which is constituted by the thickness of the film 35 and adhesive agent 41. Note that, in the case as in the second embodiment where the electrode-facing surfaces 225a (second regions) and the detection part-facing surface 225b (first region) are flush and flow of the liquid sample onto the IDT electrodes is not allowed, preferably the contact angles at the electrode-facing surfaces are 90° or more.

In the embodiments, the first region was constituted by a film or coating layer and was located in the lower part relative to the second regions. However, the first region and the second regions may be flush as well. For example, a film or a coating layer may be arranged on a cover body having a concave portion formed by the thickness of the film or coating layer in advance as well.

The pair of IDT electrodes and detection part (metal film) may be provided not only as a single set, but as two or more sets as well. For example, in the first embodiment, the widths of the metal films 55 may be made equal to those of the detection regions 23a, and a plurality of combinations of IDT electrodes and metal films may be arranged in the x-direction (flow direction of liquid sample). In this case, it is possible to fix the aptamers to one set of metal film and not fix the aptamers to another set of metal film and compare the two so as to measure the change of the SAW due to bonding of the liquid sample and the aptamers. Further, a different type of aptamers may be fixed to each metal film, and the properties or ingredients which are different for each liquid sample may be measured as well.

In the above embodiments, the explanation was given by using the term (example) of "hydrophilicity". However, as already mentioned, the sample (liquid sample) is not limited to one containing water. When the sample does not contain water, the term "amphiphilicity" may be used in place of hydrophilicity.

Note that, from the embodiments described in the present description (particularly the first, fourth, and fifth embodiments), another invention can be extracted which is characterized in that the first region facing the detection part projects to the piezoelectric substrate side more than a pair of second regions which are located on the two sides of the first region in the direction of alignment of the detection part and IDT electrodes.

In this other invention, the contact angle to the liquid sample in the first region does not always have to be smaller than the contact angles to the liquid sample in the second regions. In this other invention, for example, the height from the piezoelectric substrate to the first region becomes lower than the height from the piezoelectric substrate to the second region, therefore the capillary phenomenon can be made easier to occur in the first region than the second region.

REFERENCE SIGNS LIST

1 . . . SAW sensor (surface acoustic wave sensor), 23 . . . piezoelectric substrate, 23a . . . detection region (detection part), 25 . . . cover, 25a . . . surface facing electrode, 25b . . . surface facing detection part (first region), 45 . . . first IDT electrode, and 47 . . . second IDT electrode.

The invention claimed is:

1. A sensor, comprising:
   a substrate;
   a detection part disposed on an upper surface of the substrate, the detection part being configured to detect a detection object which is contained in a sample which flows in a first passage; and
   a cover configured to cover the detection part through a space which is a part of the first passage, wherein
   a lower surface of the cover comprises
      a first region facing at least a portion of the detection part, and
      a pair of second regions at both sides relative to the first region in a direction crossing a flow direction of the first passage, and
   the first region has a contact angle to the sample smaller than that of the pair of second regions.

2. The sensor according to claim 1, further comprising a pair of electrodes at both sides relative to the detection part in the direction crossing the flow direction.

3. The sensor according to claim 2, further comprising a protective member covering the detection part and the pair of electrodes, wherein
   the space is configured on the protective member.

4. The sensor according to claim 2, wherein the pair of second regions face the pair of electrodes, respectively.

5. The sensor according to claim 1, wherein the contact angle of the first region to the sample is less than 90°.

6. The sensor according to claim 1, wherein
   the cover comprises
      a base material having the first region and the pair of said second regions, and
      a film laminated on the first region of the base material, and
   a lower surface of the film has a contact angle to the sample smaller than that of the pair of second regions.

7. The sensor according to claim 1, wherein
   the cover comprises
      a base material having the first region and the pair of said second regions, and
      a coating layer on a surface of the first region of the base material, the coating layer comprising a surface having a contact angle to the sample smaller than that of a surface of the base material, and
   the coating layer is not on surfaces of the pair of second regions.

8. The sensor according to claim 1, wherein the pair of second regions project downward more than the first region.

9. The sensor according to claim 1, wherein the first region projects downward more than the pair of second regions.

10. The sensor according to claim 1, wherein the cover comprises a port opening outward at a side surface of the cover while communicating with the space.

11. The sensor according to claim 1, wherein the cover comprises a hole opening toward the space at the lower surface of the cover while communicating with outside of the cover.

12. The sensor according to claim 1, wherein the cover comprises a wall located on a side of the space while located on the substrate.

13. The sensor according to claim 1, further comprising a package holding the substrate and the cover therein; and
   a second passage configured to connect outside of the package and the space.

14. The sensor according to claim 13, wherein
   an upper surface of the second passage is located in a same plane as the first region, and
   the upper surface of the second passage has a contact angle to the sample smaller than that of the pair of second regions.

15. The sensor according to claim 1,
   further comprising a lower layer portion having an upper surface on which the substrate is located,
   wherein
   the cover comprises
      a middle layer portion on the lower layer portion, the middle layer portion being located at a lateral portion of the substrate, and
      an upper layer portion on the middle layer portion, the upper layer portion being above the substrate and covering the substrate.

16. The sensor according to claim 15, wherein
   the middle layer portion comprises
      a first layer on the lower layer portion, and
      a second layer on the first layer, and
   in the direction crossing the flow direction, the first layer is closer to the substrate than the second layer.

17. The sensor according to claim 16, wherein,
   the first layer comprises an exposed surface in an upper surface thereof, the exposed surface being exposed from the second layers, the exposed surface having a contact angle to the sample which is smaller than that of the pair of second regions and which is larger than that of the first region.

18. The sensor according to claim 1, comprising a plurality of the detection parts, wherein
   the first region faces at least a portion of the plurality of the detection parts.

19. The sensor according to claim 1, wherein the detection part comprises a metal film on which an aptamer is fixed.

20. A sensor, comprising:
   a substrate;
   a detection part disposed on an upper surface of the substrate, the detection part being configured to detect a detection object which is contained in a sample which flows in a first passage; and
   a cover configured to cover the detection part through a space which is a part of the first passage, wherein
   a lower surface of the cover comprises
      a first region facing at least a portion of the detection part, and
      a pair of second regions at both sides relative to the first region in a direction crossing a flow direction of the first passage, and
   the pair of second regions are exposed to the space but project downward more than the first region.

21. A sensor, comprising:
   a substrate;
   a detection part disposed on an upper surface of the substrate, the detection part being configured to detect a detection object which is contained in a sample which flows in a first passage; and
   a cover configured to cover the detection part through a space which is a part of the first passage, wherein
   a lower surface of the cover comprises
      a first region facing at least a portion of the detection part, and a pair of second regions at both sides relative to the first region in a direction crossing a flow direction of the first passage, and the first region projects downward more than the pair of second regions.

* * * * *